(12) United States Patent
Werk et al.

(10) Patent No.: US 10,773,838 B2
(45) Date of Patent: Sep. 15, 2020

(54) CLOSING A CHAMBER OF A CONTAINER FOR A PHARMACEUTICAL PRODUCT

(71) Applicant: Hoffmann-La Roche Inc., Little Falls, NJ (US)

(72) Inventors: Tobias Werk, Riehen (CH); Jörg Lümkemann, Lörrach (DE); Hanns-Christian Mahler, Lörrach (DE); Tom Kissling, Riehen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 445 days.

(21) Appl. No.: 15/531,884

(22) PCT Filed: Dec. 4, 2015

(86) PCT No.: PCT/EP2015/078607
§ 371 (c)(1),
(2) Date: May 31, 2017

(87) PCT Pub. No.: WO2016/087627
PCT Pub. Date: Jun. 9, 2016

(65) Prior Publication Data
US 2017/0259948 A1    Sep. 14, 2017

(30) Foreign Application Priority Data
Dec. 5, 2014   (EP) .................................... 14196514

(51) Int. Cl.
*B65B 7/28*     (2006.01)
*B65D 51/00*    (2006.01)
(Continued)

(52) U.S. Cl.
CPC ........... *B65B 7/2821* (2013.01); *A61M 5/008* (2013.01); *B65B 3/003* (2013.01); *B65B 55/027* (2013.01);
(Continued)

(58) Field of Classification Search
CPC ....... B65B 3/003; B65B 3/006; B65B 7/2821; B65B 55/027; A61M 5/008; B65D 51/26;
(Continued)

(56) References Cited

U.S. PATENT DOCUMENTS 4,230,231 A  * 10/1980  Burnett .............. B65D 39/0047
                                                         215/277
4,286,389 A     9/1981  Ogle
(Continued)

FOREIGN PATENT DOCUMENTS

DE         2209311 A1  *  9/1973  ............. B67B 1/005
JP      H05-035325 U     5/1993
(Continued)

OTHER PUBLICATIONS

International Search Report and Written Opinion, issued in PCT/EP2015/078607, dated Mar. 17, 2016.
(Continued)

*Primary Examiner* — Stephen F. Gerrity
*Assistant Examiner* — Joshua G Kotis
(74) *Attorney, Agent, or Firm* — Medler Ferro Woodhouse & Mills PLLC; Teresa Medler

(57) ABSTRACT

A device (1) for closing a chamber of a container having an opening for accessing the chamber comprises a plunger, a plunger seat (11), a container carrier (13) and a spacer (12). The plunger seat (11) releasably holds the plunger in a predefined alignment. The container carrier (13) is arranged to be connected to the container in a predefined position and alignment in relation to the opening of the container. The spacer (12) is arranged to position and align the plunger seat (11) adjacent to and distant from the container carrier (13) such that the opening of the container is open when the container is connected to the container carrier (13).

7 Claims, 16 Drawing Sheets

(51) Int. Cl.
    *B67B 1/04*    (2006.01)
    *B65B 3/00*    (2006.01)
    *B65B 55/02*    (2006.01)
    *B65D 25/10*    (2006.01)
    *A61M 5/00*    (2006.01)

(52) U.S. Cl.
    CPC ........... *B65D 25/108* (2013.01); *B65D 51/00* (2013.01); *B67B 1/04* (2013.01)

(58) Field of Classification Search
    CPC .... B65D 51/241; B65D 51/242; B65D 41/28; B65D 51/002; B67B 1/04; B67B 1/045
    USPC .................. 53/319, 321–324, 328, 471, 489; 215/247
    See application file for complete search history.

(56) References Cited

U.S. PATENT DOCUMENTS

| | | | | |
|---|---|---|---|---|
| 5,299,408 A | * | 4/1994 | Dupont | B67B 1/04 53/109 |
| 5,377,854 A | * | 1/1995 | Cusack | B65D 51/241 215/307 |
| 5,519,984 A | | 5/1996 | Beussink et al. | |
| 5,718,348 A | * | 2/1998 | Manera | B65D 41/28 215/249 |
| 5,819,964 A | * | 10/1998 | Grimard | B65D 51/002 215/249 |
| 6,029,836 A | * | 2/2000 | Ligeras | B65D 41/08 215/296 |
| 6,223,408 B1 | * | 5/2001 | Vetter | B65B 3/003 29/234 |
| 2005/0086830 A1 | | 4/2005 | Zukor et al. | |
| 2005/0172580 A1 | * | 8/2005 | Krulitsch | B67C 3/004 53/471 |
| 2010/0224632 A1 | * | 9/2010 | Aneas | B65D 51/002 220/315 |
| 2011/0030320 A1 | * | 2/2011 | Blumenstock | B65B 7/2821 53/485 |
| 2012/0118903 A1 | * | 5/2012 | Norton | B01L 3/0293 220/755 |
| 2012/0204683 A1 | * | 8/2012 | Nazikian | B67B 1/045 81/3.29 |
| 2012/0248057 A1 | | 10/2012 | Bogle et al. | |
| 2013/0213924 A1 | * | 8/2013 | Vrijens | B65D 51/002 215/355 |
| 2015/0283030 A1 | * | 10/2015 | Skufca | A61J 1/062 604/413 |
| 2017/0341784 A1 | * | 11/2017 | Lumkemann | A61J 1/062 |

FOREIGN PATENT DOCUMENTS

| | | |
|---|---|---|
| JP | H11-501893 H1 | 2/1999 |
| WO | 2011/019605 | 2/2011 |

OTHER PUBLICATIONS

Notice of Reasons for Rejection dated Feb. 4, 2020 in corresponding Japanese Application No. 2017-528913.

* cited by examiner

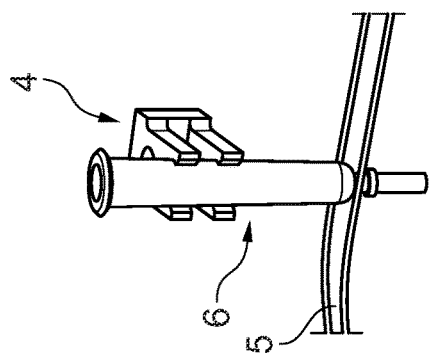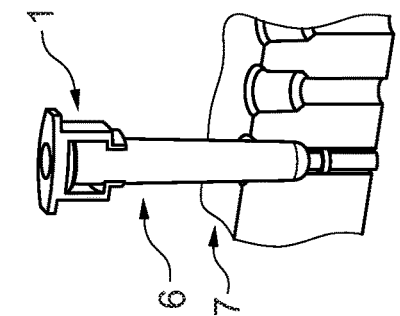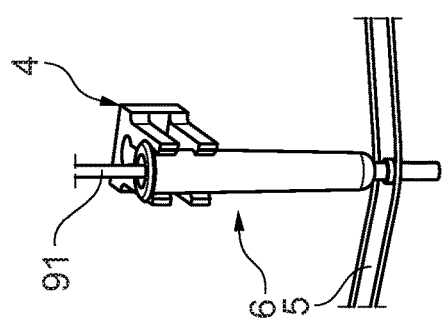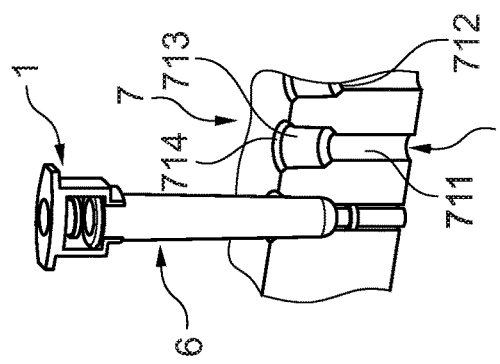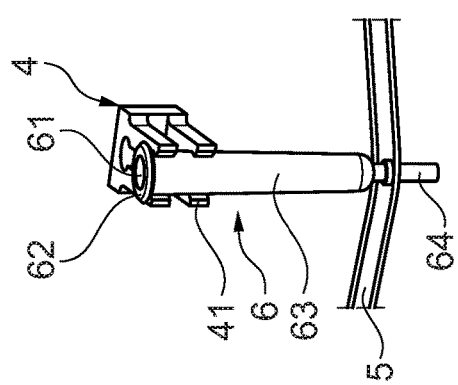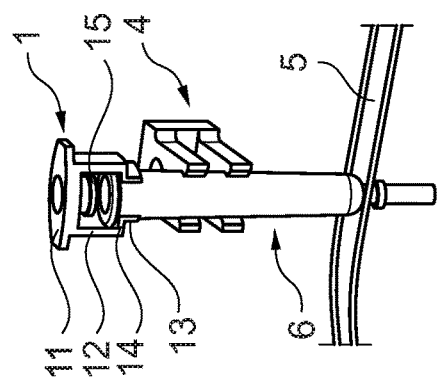

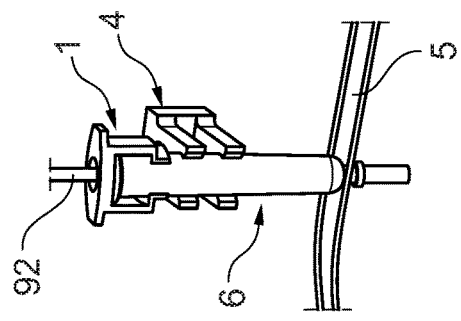
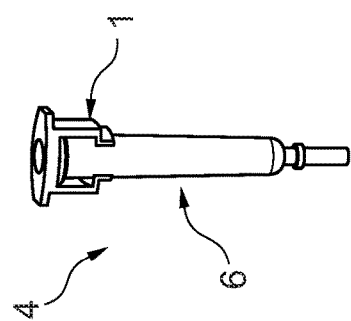
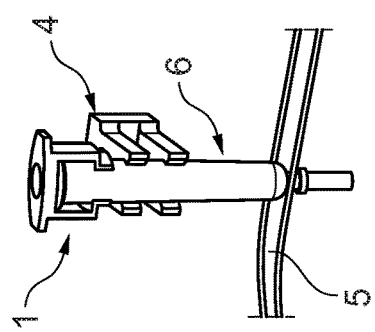
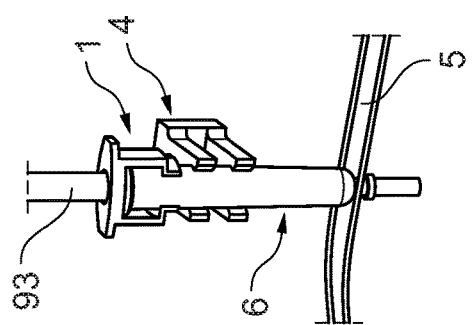

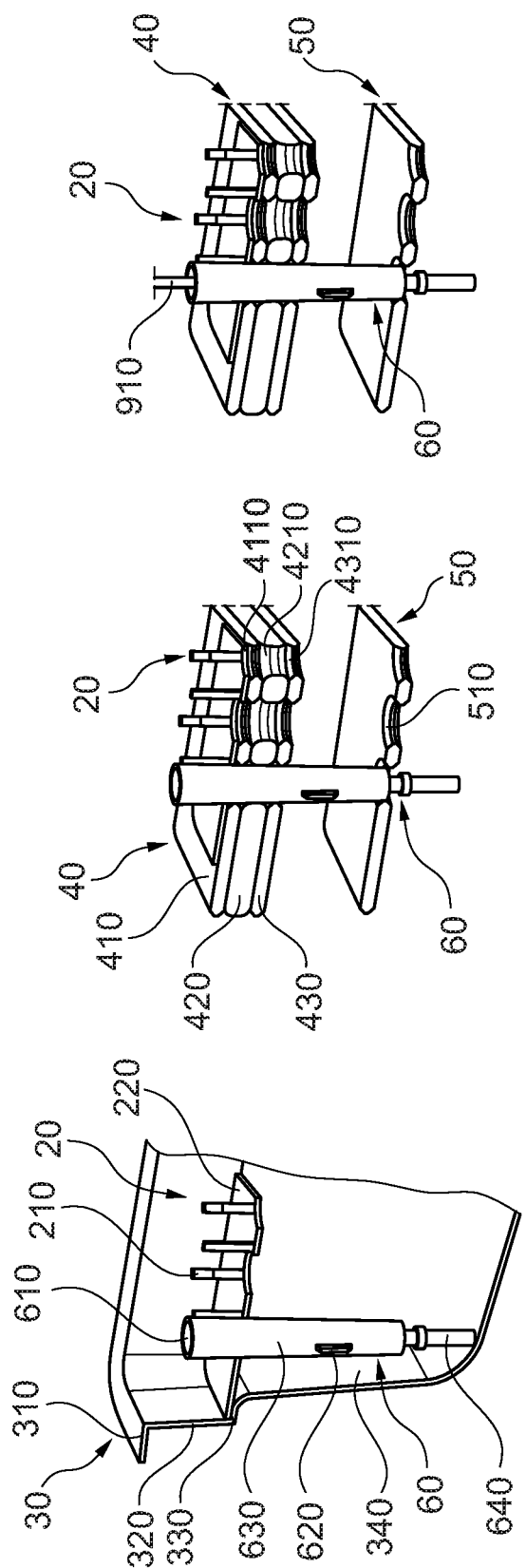

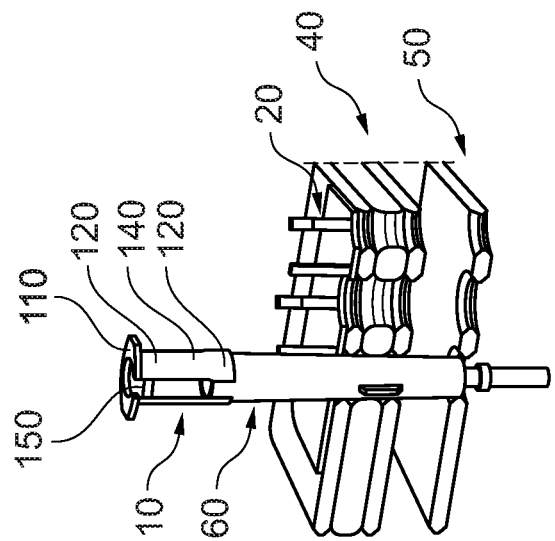
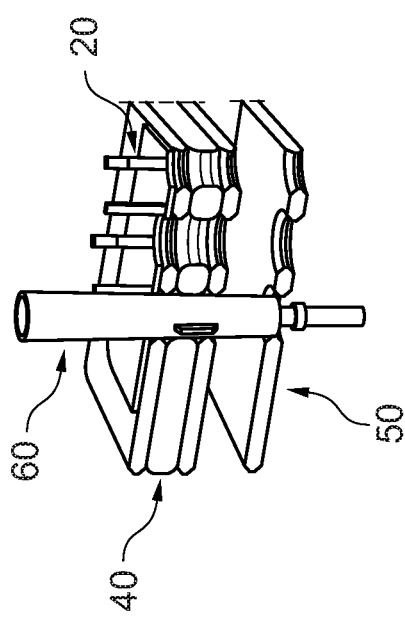
Fig. 4AE'
Fig. 4AD'

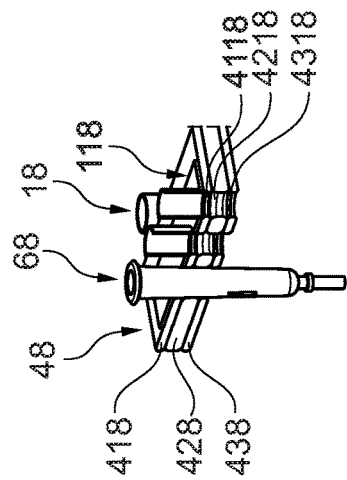
Fig. 6A"
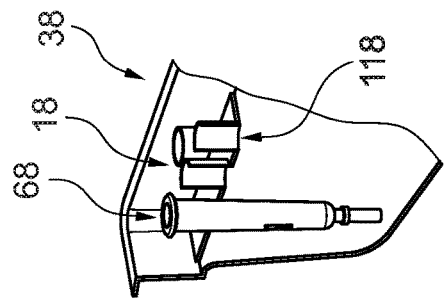
Fig. 6B"
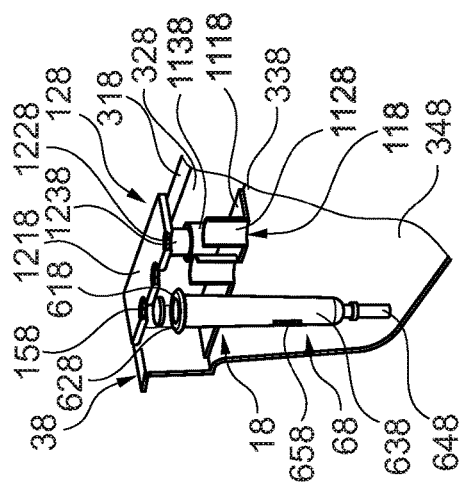
Fig. 6C"
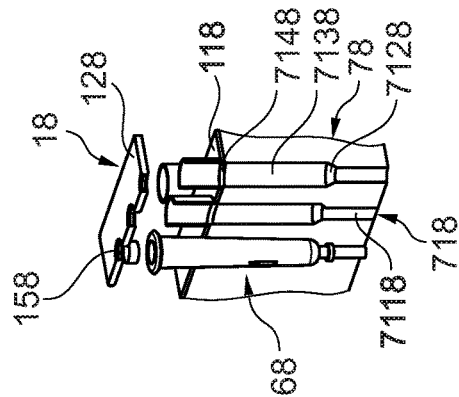
Fig. 6D"
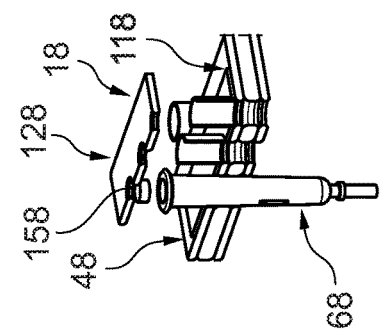
Fig. 6E"
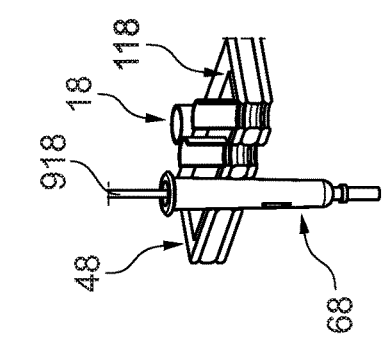
Fig. 6F"

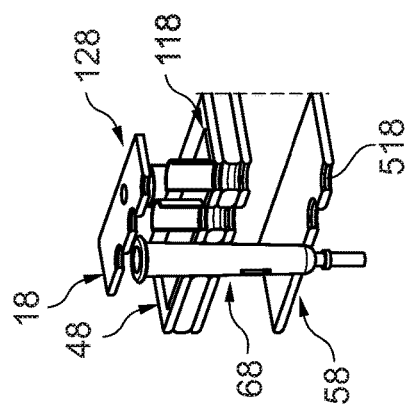
Fig. 6G"
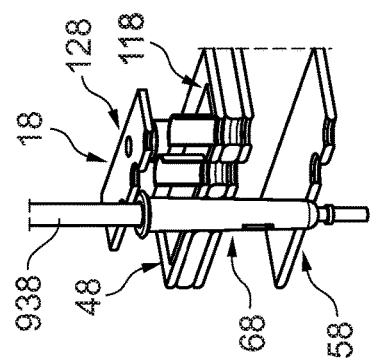
Fig. 6H"
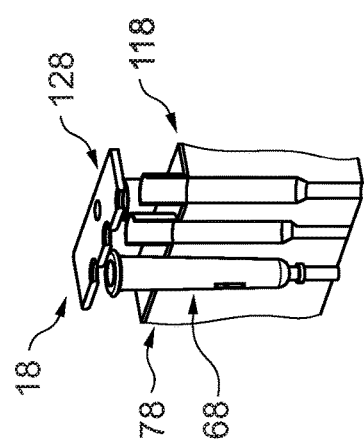
Fig. 6I"
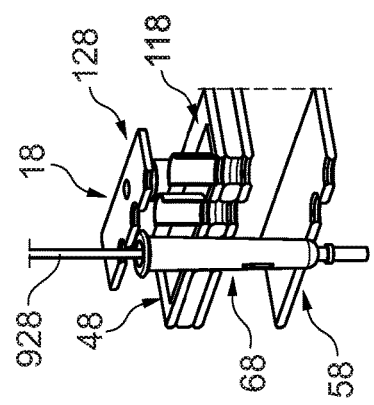
Fig. 6J"

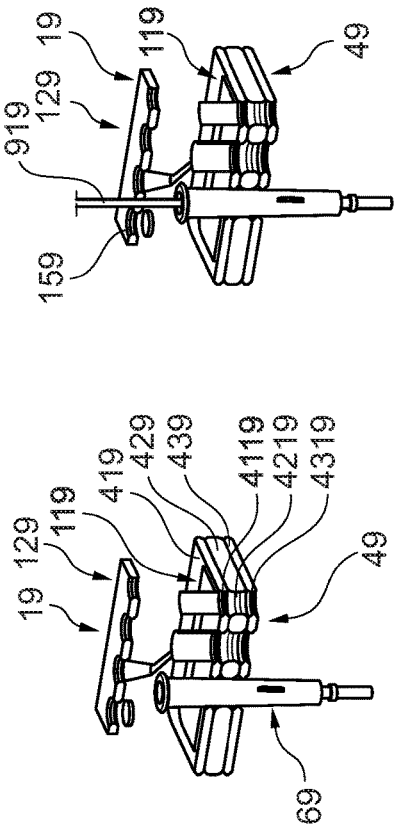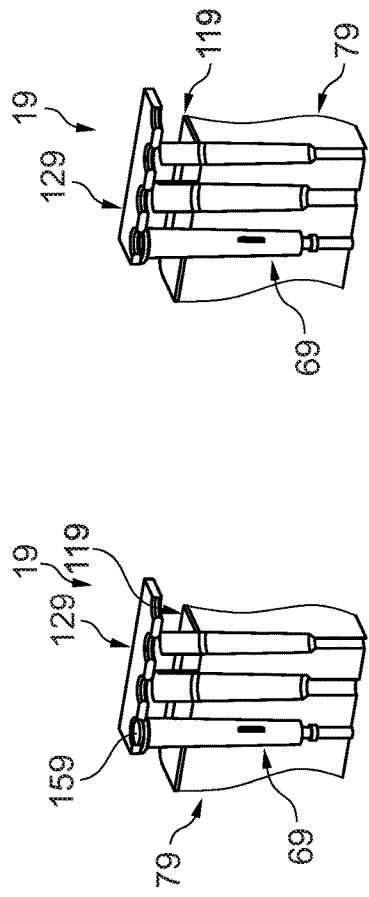

CLOSING A CHAMBER OF A CONTAINER FOR A PHARMACEUTICAL PRODUCT

TECHNICAL FIELD

The present invention relates to a device for closing a chamber of a container having an opening for accessing the chamber. Such devices can be used in processes of preparing pharmaceutical products and containers filled with pharmaceutical products.

BACKGROUND ART

Many pharmaceutical products, pharmaceutical substances or simply pharmaceuticals are processed and/or applied in liquid form. For this, the liquid pharmaceuticals are filled into containers such as in vials, syringes or the like. Also, many pharmaceuticals and particularly biopharmaceuticals which frequently are highly unstable in liquid form are often provided in a lyophilized form in which they are essentially more stable and robust compared to their liquid forms. The lyophilized pharmaceuticals can also be filled and provided in containers. Before being applied to patients, they are reconstituted or solved in a diluent or similar liquid.

For allowing injection such as subcutaneous, intramuscular, intradermal or intravitreal injection of a pharmaceutical product, which often is most efficient and preferred, pharmaceuticals can be provided directly in syringes such as in staked-in needle pre-filled syringes ready for being applied. In cases where lyophilised pharmaceuticals are involved dual chamber syringes are commonly used in which one chamber houses the lyophilised pharmaceutical and the other chamber the diluent. When being applied, an activation rod is pushed into the double chamber syringe in two steps. In a first step, it is pushed far enough for bringing the diluent and pharmaceutical together and in a second step it is completely pushed in order to provide the liquidized or solved pharmaceutical out of the needle.

For closing containers filled with pharmaceuticals, it is known to use rubber plungers. Thereby, a plunger is usually arranged into an opening of a container for sealing it. On an industrial level such plungers usually are automatically pushed or sucked into the openings of the containers after the pharmaceutical is arranged inside the chambers of the containers. Particularly since the containers and the plungers have to be kept uncontaminated, closing the containers is often performed in a sterile environment. However, namely on an industrial level the closing of containers in a sterile manner when preparing the containers comprising the pharmaceutical can be cumbersome and cause an undesirable effort.

In particular, closing containers in the process of preparing lyophilized pharmaceuticals inside the containers can be comparably complicated. Notably, when lyophilized pharmaceuticals are prepared and packaged in dual chamber syringes closing the syringes by providing plungers into their openings within the process of preparing the syringes and the pharmaceuticals can be comparably difficult and causing comparably high costs. However, since the lyophilized pharmaceuticals in double chamber syringes can be comparably simply processed such as transported, stocked, sold, applied and the like, efficient preparation of double chamber syringes is desired.

Therefore, there is a need for a device or system allowing for efficiently closing containers such as double chamber or other syringes within a process of preparing the containers wherein, for example, such process can comprise lyophilisation of a product inside the container.

DISCLOSURE OF THE INVENTION

In particular, the invention deals with a device for closing a chamber of a container having an opening for accessing the chamber. The device comprises a plunger, a plunger seat, a container carrier and a spacer. The plunger seat releasably holds the plunger in a predefined alignment. The container carrier is arranged to be connected to the container in a predefined position and alignment in relation to the opening of the container. The spacer is arranged to predefine a position and alignment of the plunger seat in relation to the container carrier. In a predefined distant position of the device, the plunger seat is located distant from the opening of the container when the container is connected to the container carrier such that the opening of the container is open. In a predefined near position of the device, the plunger seat is arranged adjacent to the opening of the container when the container is connected to the container carrier such that the plunger is providable into the opening of the container for closing the container.

In connection with the plunger seat the term "releasably" can relate to a connection between the plunger seat and the plunger which is strong enough in order that the plunger seat carries the plunger and is slight enough such that the plunger can easily be separated from the support. In particular, in accordance with the invention the plunger seat can hold the plunger such that it carries the plunger and at the same time the plunger can conveniently be released from the plunger seat for being provided to the container without being impaired or damaged or the like. For example, such connection can be embodied by holding the plunger by friction in the plunger seat.

The term "predefined" as used herein, generally, relates to arrangements, positions or situations for which the device or particular features thereof are embodied. For example, the device can have particular means or measures for clearly target a particular position or situation. By such means the device can predefined such particular position or situation. The term is to distinguish from not being clearly defined such as a position which might by accident or within a unclear movement be achieved. For example, if a plunger is manually provided into a container and thereby being transferred through the distant position defined herein such positioning is not predefined.

More particular, the term "predefined" in connection with the distant and near positions of the device can relate to an arrangement of the device allowing to ensure that the distant and near positions are well achieved. In particular, the device can be embodied with particular means as described in more detail below by way of exemplary embodiments for exactly providing the near and distant positions such that these positions are well defined. Thereby, such means can allow either a connection of the plunger seat and the container carrier which is adjustable between the distant and near positions. Or, such means can allow a corresponding connection of the device and the container itself.

The term "predefined alignment" with respect to the plunger held by the plunger seat of the support can relate to a rotational and directional arrangement of the plunger. In particular, the rotational and directional arrangement can be predefined or adjusted for being further processed or to a specific aim. This can allow the plunger to be easily provided into the opening of the container for closing it. In particular, the term can relate to an alignment of the plunger allowing for straightly pushing or sucking it into the opening of the container when the container is connected to the container carrier.

The term "predefined position and alignment" with respect to the container carrier can particularly relate to an arrangement ensuring that the opening of the container is suitably located and suitably adjusted or rotated and directed. Together with the arrangement of the plunger seat and the spacer, this allows for well defining the position of the plunger in relation to the opening of the container such that the plunger can be easily provided into the opening of the container for closing it. Particularly, the location and adjustment of the plunger seat can allow for straightly pushing or sucking the plunger into the opening of the container.

The term "distant" in connection with the plunger seat in relation to the opening of the container connected to the container carrier can relate to an arrangement of the plunger in which on one hand it does not contact the opening of the container or an edge of it and on the other hand there is a free space in between the plunger and the opening. Like this, it can be assured that the opening is kept open and accessible.

The term "adjacent" in connection with plunger seat in relation to the opening of the container connected to the container carrier can relate to an arrangement in which the plunger seat contacts or nearly contacts the container at its opening. It can relate to an arrangement in which the plunger held in the plunger seat is close enough to the opening for being efficiently provided into the container. In such arrangement the opening of the container may not or not fully be open.

The term "open" in connection with the container being connected to the container connection and the plunger being held by the plunger seat can relate to an accessibility of the chamber of the container from its outside. For example, when the container is open substances can be filled into the chamber of the container through its opening or gases such as steam can escape the chamber, e.g. during lyophilisation.

The container can be suitable for providing a substance intended for lyophilisation. For example, it can be a vial or a syringe. In particular, it can be a double chamber syringe which, in a finally prepared status, has one chamber containing a loyphilisate or freeze-dried substance or product and another chamber containing a reconstitution medium such as a liquid diluent.

The device according to the invention can particularly be beneficial in processes of preparing chemical or biological pharmaceutical substances in a ready-to-use form. In particular, it can increase efficiency of packaging the substances in containers, e.g. in a preparation process including drying such as freeze-drying. The terms "pharmaceutical substance", "pharmaceutical product", "pharmaceutical" are synonymously used herein. Also, the terms "freeze-drying" and "lyophilizing" are used synonymously herein.

As explained in more detail below with respect to preferred embodiments, the plunger seat, the container carrier and the spacer can be embodied in one single piece for example made of a plastic material. Thereby, its container carrier, plunger seat and spacer can be fixedly arranged in relation to each other. Alternatively, the plunger seat together with a first portion of the spacer can form a first single piece of the device and the container carrier together with a second portion of the space a second single piece of the device.

The device, can be made of any suitable material wherein for pharmaceutical application it can particularly be made of a sterilisable material. Such sterilisable material can for example be a plastic material which can be additionally beneficial with respect to manufacturing costs and flexibility.

The device according to the invention allows for efficiently closing containers filled with pharmaceuticals. It can be obtained in a pre-sterilized form which allows for easily integrating it in a process of preparing pharmaceuticals including packaging. Since the plunger seat aligns the plunger and the container carrier aligns and positions the opening of the container in relation to the plunger seat the plunger can efficiently be provided into the opening for closing it. Further, since the spacer between the container carrier and the plunger seat positions and aligns the plunger seat adjacent to or distant from the container carrier the opening of the container is open when the device is in the distant position, e.g. when the container is connected to the container carrier. Thereby, the pharmaceutical inside the container can be processed in a comparably unimpaired manner wherein the device and the container form a unit during plural steps of the preparation process. In particular, such arrangement allows for efficiently lyophilising the pharmaceutical inside the container wherein the device is connected to the container such that it is not necessary to change the assembly after lyophilisation for closing the container. This allows for providing an efficient process of preparing containers comprising pharmaceuticals, particularly, when such process includes lyophilisation of the pharmaceutical.

Preferably, the plunger is made of an elastically deformable material, e.g., an elastic plastic material such as butyl or a rubber material. Such an elastically deformable material allows for the plunger to tightly close the container. In particular, when being pushed or sucked into the opening of the container the plunger can be compressed such that due to its elasticity it presses itself against and tightly connects to the side wall of the container or a neck thereof.

Preferably, the plunger seat comprises a through-hole dimensioned to releasably hold the plunger when being arranged in the though-hole. Thereby, the through hole can be sized to hold the plunger by friction. Alternatively or additionally, the interior of the through-hole can be equipped with a bulge which corresponds to ribs of the plunger. In particular, one plunger rib resides on the bulge and, as the plunger is elastic, the device is releasable holding the plunger. Such an arrangement of the plunger seat is particularly suitable for plungers being made of an elastically deformable material as mentioned hereinbefore. It allows for a comparably easy construction of the plunger seat. In particular no clamping means, other holding means or the like are necessary.

In a first preferred embodiment, the device comprises a support having the plunger seat, the container carrier and the spacer between the plunger seat and the container carrier, wherein the container carrier comprises a clamping portion for clamping a section of the container adjacent to its opening and the container carrier passes over into the spacer via a step arranged for contacting an edge of the opening of the container. In particular, in the first embodiment the support can be a one-piece construction whereas the plunger forms another separate piece. The step can form a right angle with the at least one cylinder segment of the clamping portion and the spacer. It can also form any other angle or a curve without a particular angle.

Thereby, the clamping portion of the container carrier preferably comprises at least one cylinder segment between which the section of the container adjacent to its opening is clampable. Such a clamping mechanism allows for precisely and safely connect the container. Also, it allows for an efficient manufacture of the device and particularly its container carrier.

The spacer of the support preferably comprises at least one cylinder segment connecting the clamping portion of the container carrier via the step and the plunger seat. The at least one cylinder segment of the spacer can also be a full cylinder. Such a spacer with at least one cylinder segment can be efficiently embodied particularly when the container carrier comprises the at least one cylinder segment. In such an embodiment, the number of the cylinder segments of the spacer advantageously corresponds to the number of the cylinder segments of the clamping portion of the container carrier. In particular, each cylinder segment of the spacer can pass over to one of the cylinder segments of the clamping portion of the container carrier via a section of the step.

In a variant of the first preferred embodiment, each of the at least one cylinder segment of the clamping portion of the container carrier is connected to one of the at least one cylinder segments of the spacer via the step and the at least one cylinder segment of the clamping portion has an inner diameter which is smaller than an inner diameter of the at least one cylinder segment of the spacer.

The inner diameter of the at least one cylinder segment of the clamping portion can particularly be slightly smaller than the outer diameter of the section of the container adjacent to its flange portion. Since the inner diameter of the at least one cylinder segment of the clamping portion is smaller, the step extends outwardly from the clamping portion. Like this the container carrier and particularly its clamping portion can be clamped on the container by elastically deforming its at least one cylinder segment in an outward direction. The inner diameter of the at least one cylinder segment of the spacer can be dimensioned such that the flange portion of the container fits inside. I.e. the inner diameter of the at least one cylinder segment is identical or bigger than the outer diameter of the flange portion of the container.

Thereby, the step of the device preferably is arranged for contacting the edge which has a finger flange portion formed around the opening of the container. Such an arrangement of the step allows the device being applied with containers having a finger flange such as syringes having a finger flange near its opening for arranging the fingers while pushing the activation rod.

In another variant of the first preferred embodiment, each of the at least one cylinder segment of the clamping portion of the container carrier is connected to one of the at least one cylinder segment of the spacer via the step and the at least one cylinder segment of the spacer has an inner diameter which is smaller than an inner diameter of the at least one cylinder segment of the clamping portion.

The inner diameter of the at least one cylinder segment of the clamping portion can particularly be slightly smaller than the outer diameter of the section of the container adjacent to the opening. Like this, the container carrier and particularly its clamping portion can be clamped on the container by elastically outwardly deforming its at least one cylinder segment. Since the inner diameter of the at least one cylinder segment of the spacer is smaller the step extends inwardly from the clamping portion. The container can be pushed into the at least one cylinder segment of the clamping portion of the container carrier until the edge of the opening of the container abuts the edge of the support. Like this, the support can be precisely connected to the container.

Within the first preferred embodiment, the plunger seat preferably comprises at least one protrusion laterally projecting over the spacer. Such a protrusion can be used as a finger flange being embodied in the support. For example, such an embodiment can be used with a syringe not having an own finger flange. It allows for providing the container such as a syringe with a finger flange which, e.g., can be necessary for applying an activation rod into the syringe for providing the substance or product out of the syringe. The protrusion can also be used in an auto-injector. Also, it allows for efficiently handling the device such as, e.g., for removing the device at the end of processing.

In a second preferred embodiment, the device has a support and a holder wherein the support comprises the plunger seat and a support part of the spacer, the holder comprises the container carrier and a holder part of the spacer, and the support part of the spacer and the holder part of the spacer are arranged to interengage to be connected in the distant position and to be connected in the near position. In this context the holder and support parts are formed to be capable of being connected in the distant position as well as in the near position whereas they are only connected in one of the positions at a time.

The term "interengage" in this context relates to the support and holder parts of the spacer interacting in a predefined manner. Particularly, the support and holder parts can be fixedly or releasably connected to each other. Thereby, the arrangement of the support and holder parts of the support allows to position and align the plunger seat and the container carrier in a predefined manner. The spacer can be arranged such that the support part and the holder part are guided from the distant position to the near position.

In a variant of the second preferred embodiment, the holder part of the spacer and the support part of the spacer interengage by forming a snap-in connection. For example, the support part of the spacer can have at least one elastically movable cylinder segment with a bulge on its outer surface and the holder part of the spacer can be embodied as a hollow cylinder having a sidewall with a thicker section and a thinner section. In such an embodiment of the spacer, the support part can snap-in the holder part by pressing the at least one cylinder segment into the hollow cylinder until the bulge engages behind the thicker section of the hollow cylinder. In this position the support part is connected to the holder part, e.g. in the near position. As other similar embodiments, the support and holder parts can also oppositely be formed, i.e. the holder part has the at least one cylinder segment and the support part has the hollow cylinder. Or, one of the support and holder parts can be embodied as rod with a bulge on its circumference and the other one of the support and holder parts is correspondingly embodied as flexible hollow cylinder having a sidewall or sidewall segments of varying thicknesses.

The snap-in connection formed by the holder part of the spacer and the support part of the spacer preferably is arranged to connect the holder part of the spacer and the support part of the spacer in plural distinct positions. Such multi-position snap-in can be achieved in a spacer as described hereinbefore, i.e. comprising the support part having at least one elastically movable cylinder segment with a bulge on its outer surface and the holder part embodied as a hollow cylinder having the sidewall with the thicker section and the thinner section, by providing a groove in the thicker section of the sidewall. In such an embodiment of the spacer, the support part can snap-in the holder part in at least two positions. In one position, e.g. the distant position, the bulge of the support section is arranged in the groove of the thicker section of the hollow cylinder of the holder section and in another position, e.g., the near position, the bulge engages behind the thicker section of the hollow cylinder. Again, other similar embodiments are possible as described above. Such a multi-position snap-in spacer allows for connecting the support with the holder in the distant position where the container is open and in the near position where the container is closed or nearly closed.

In another variant of the second preferred embodiment, the holder part of the spacer comprises an inclined ramp and the support part of the spacer comprises a slider, wherein the slider is movable along the ramp from the distant position in which the plunger seat of the support is distant and laterally displaced from the container carrier of the holder to the near position in which the plunger seat of the support is adjacent and straightly directed to the container carrier of the holder. The ramp can have a straight or bent surface along which the slider can move while being in contact. The term "inclined" can relate to a slant inclination of the ramp with respect to a direction the support and the holder have to be moved to each other in order in order to bring the plunger and the opening of the container together. The slider can comprise or be shaped as a post or a similar structure suitable for moving in contact with and along the ramp. The ramp and the slider allow for precisely moving the support and the holder towards each other wherein this movement is not in a straight direction but in a in direction sideways or laterally to each other. Thus, the ramp allows for moving the support and the holder towards each other and at the same time laterally offsetting the support and the holder to each other.

Thereby, the holder part of the spacer comprises a distant fastener at one end of the ramp for fastening the slider of the support part of the spacer in the distant position and a near fastener at the other end of the ramp for fastening the slider of the support part of the spacer in the near position. The distant fastener can, e.g., be embodied as a hook clamping the slider when the holder is in the distant position. The near fastener can, e.g., be formed as a recess in which the slider dropped when the holder is in the near position. The two fasteners allow for securing the holder and the support in the distant and near positions to each other. An unintentional movement can thereby be prevented.

The support preferably comprises an access through-hole which is straightly directed to the container carrier of the holder when the device is in the distant position. Such an access through-hole allows for accessing the interior of the container through the device which can increase efficiency when processing the container. In particular, a liquid or other substance can be filled into the container via the access through-hole and the proximal opening of the container wherein it is not required to remove the support.

Preferably, the support of the device has a support base plate on which the plunger seat and the support part of the spacer are arranged. Similarly, the holder preferably has a holder base plate on which the container carrier and the holder part of the spacer are arranged. Such a support base plate and/or holder base plate allows for efficiently manufacturing and handling the support within a process of preparing the container and the pharmaceutical.

Preferably, the support comprises at least one further plunger seat and the holder comprises at least one further container carrier, wherein the plunger seat and the at least one further plunger seat are located on the support in correspondence with the container carrier and the at least one further container carrier of the holder. With such an arrangement, plural nested plungers can be obtained in the support and provided to respective plural nested containers arranged in the holder. This allows for efficiently processing and preparing a plurality of container which can be desired in industrial processes.

These and other aspects of the invention will be apparent from and elucidated with reference to the embodiments described hereinafter.

BRIEF DESCRIPTION OF THE DRAWINGS

The device according to the invention is described in more detail hereinbelow by way of exemplary embodiments and with reference to the attached drawings, in which:

FIGS. 2A-2J show perspective partial views of a first embodiment of a facility for preparing a syringe using the device of FIG. 1;

FIGS. 4AA'-4AE' show perspective partial views of a second embodiment of a facility for preparing a syringe using the device of FIG. 3;

FIGS. 6A"-6J" show perspective partial views of a third embodiment of a facility for preparing a syringe using the device of FIG. 5;

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes includes various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for the reason of lucidity, if in a section of a drawing nor all features of a part are provided with reference signs it is referred to other sections of the same drawing. Like numbers in two or more figures represent the same or similar elements.

Figure 1:
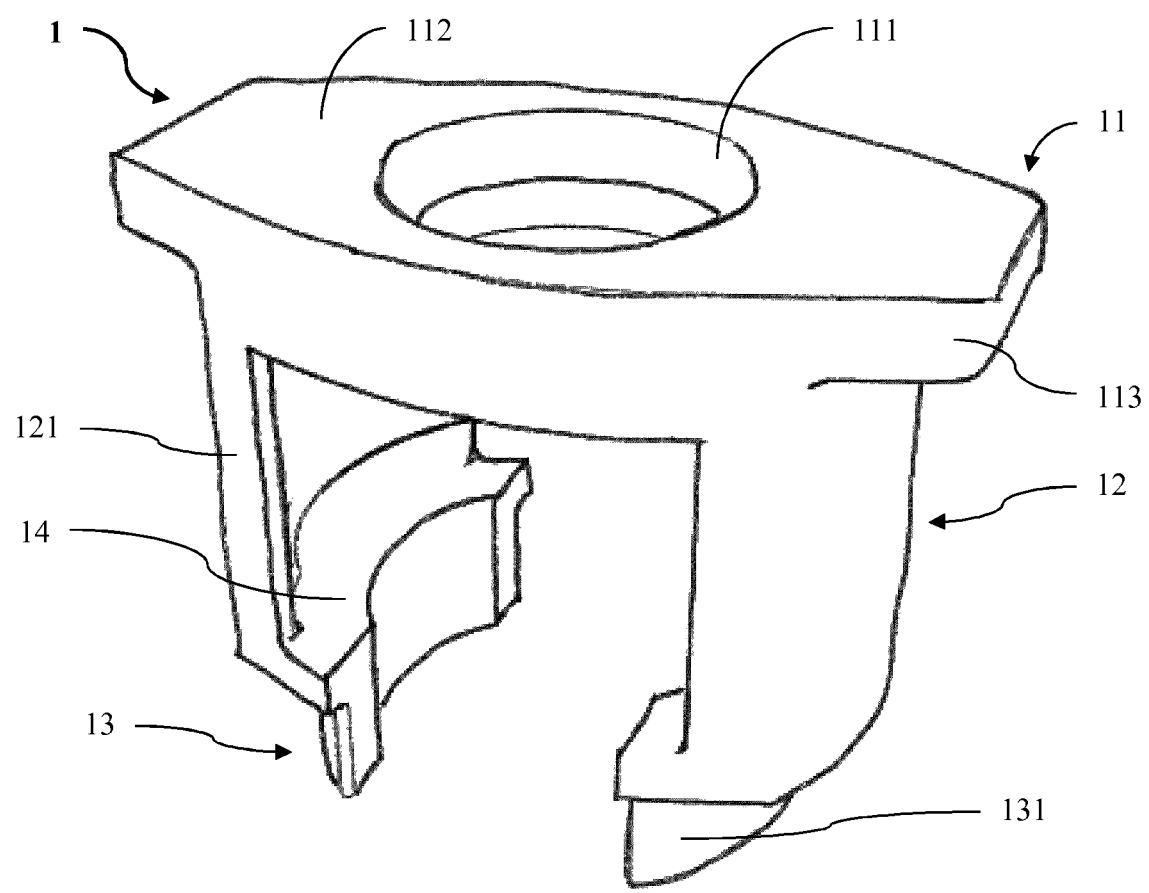
FIG. 1 shows a perspective view of a first embodiment of a device according to the invention.

In FIG. 1 a first embodiment of a device 1 according to the invention is shown. The device 1 comprises a support with a plunger seat 11, a container connector 13 as container carrier and a spacer 12 between the plunger seat 11 and the container connector 13. The support is embodied as one piece made from a plastic material. The plunger seat 11 is formed as a longitudinal plate 112 of a constant thickness having plane top and bottom surfaces. In a top view the longitudinal plate 112 widens towards its middle such that a central section of the plate 112 has the largest width. In this central section of the longitudinal plate 112 a central through-hole 111 is arranged.

On its bottom surface the longitudinal plate 112 passes over into the spacer 12. The spacer 12 comprises two opposing cylinder segments 121. The cylinder segments 121 surround a circular cylindrical interior. Each of the two lateral sections of the longitudinal plate 112 form a protrusion 113 laterally projecting over the spacer 12.

On their bottom ends each of the cylinder segments 121 of the spacer 12 pass over into a cylinder segment 131 of a clamping portion of the container connector 13 via step 14. The cylinder segments 131 of the clamping portion of the container connector 13 also surround a circular cylindrical interior. The two cylinder segments 131 of the clamping portion of the container connector 13 have an inner diameter which is smaller than an inner diameter of cylinder segments 121 of the spacer 12. Thus, the step 14 inwardly extends from the cylinder segments 121 of the spacer 12 to the cylinder segments 131 of the clamping portion of the container connector 13.

FIGS. 2A-2J shows steps of a first embodiment of a method for preparing a first embodiment of a double chamber staked-in needle syringe 6 as container. The first method is implemented in a first embodiment of a facility for preparing the syringe 6.

The syringe 6 has a distal end side, a proximal end side opposite to the distal end side and a cylindrical body portion 63 with an interior between the distal end side and the proximal end side. A distal opening provided with a needle is arranged at the distal end side of the syringe 6. The needle is covered and protected by a rigid needle shield 64.

The proximal end side of the syringe 6 has a proximal opening 61 for accessing the interior of the body portion 63 surrounded by a finger flange 62. The distal end side, the body portion 63 and the proximal end side with its finger flange 62 are integrally made of glass, i.e. are one piece.

In the step of FIG. 2A of the first method the syringe 1 is arranged in a respective seat of a holder 4 of the first facility. The seat of the holder 4 has two parallel supporting arms 41 which receive the body portion 61 of the syringe 6 in a vertical alignment in which the proximal opening 61 is at a top end of the syringe 6 and the rigid needle shield 64 is at a bottom end of the syringe 6. The syringe 6 is abutting with its finger flange 62 onto the top end of the upper supporting arm 41 of the holder 4. Thereby, the syringe 6 is vertically hanging between the supporting arms 41 of the holder.

Below the distal end side of the syringe 6 two parallel guiding rails 5 of the first facility are arranged. The rigid needle shield 64 of the syringe 6 extends downwardly through the guiding rails 5. The two guiding rails 5 have a distance from each other suitable for the rigid needle shield 64 to fit in between or to pass through but not for the body portion 63 of the syringe 6.

In the step of FIG. 2B of the first method the holder 4 together with the syringe 6 is transferred along the guiding rails 5 by a transporter of the facility to a feeding station of the first facility. There a substance such as a liquid pharmaceutical substance or particularly a liquid biopharmaceutical substance is fed into the interior of the syringe 6. For this purpose a discharge pipe of a substance dosing feeder 91 of the first facility is entered through the proximal opening 61 into the interior of the syringe 6. Then the substance is filled into the interior of the syringe 6 wherein the syringe 1 is aligned by the holder 4 and the guiding rails 5 in order to allow for preventing leakage and contamination. After feeding, the substance is lying on the bottom of the interior of the syringe 6, i.e. at the distal end side of the syringe 6.

In the step of FIG. 2C the syringe 1 and the holder 4 are further traveled along the guiding rails 5 by the transporter of the facility. The guiding rails 5 are raising such that the distance between the guiding rails 5 and the holder 4 decreases. Since the body portion 63 of the syringe 6 does not fit between the guiding rails 5 the distal end side of the body portion 63 abuts onto the guiding rails 5. Like this the syringe 6 is lifted such that the finger flange 62 is distant from the holder 4.

As shown in the step of FIG. 2D, in this lifted position the support of the device 1 is clipped on the syringe 6. Inside the through-hole 111 of the plunger seat 11 of the support a rubber plunger 15 of the device 1 is arranged. The through-hole 111 is dimensioned to releasably hold the plunger 15 by friction. Thereby, the plunger 15 extends the through-hole 111 downwardly to a certain extent.

The clamping portion of the container connector 13 and in particular its cylinder segments 131 clamp the body portion 63 of the syringe 6 adjacent to its finger flange 62, i.e. at a section of the syringe 6 adjacent to its proximal opening 61. The step 14 of the support of the device 1 contacts an edge of the finger flange 62 of the syringe 6. The inner diameter of the two cylinder segments 131 of the clamping portion is slightly smaller than the outer diameter of the body portion 63 of the syringe 6. Thus, for the syringe 6 being arranged between the two cylinder segments 131 the clamping portion has to be elastically outwardly bent such that it is tensioned. Like this the body portion 63 is attached in between the cylinder segments 131 of the container connector 13.

The inner diameter of the cylinder segments 121 of the spacer 12 are dimensioned such that the finger flange 62 of the syringe 6 fits in between. I.e. the inner diameter of the cylinder segments 121 of the spacer 12 is identical or slightly bigger than the outer diameter of the finger flange 62 of the container 6.

Due to the height of the spacer 12 of the support of the device 1 the plunger 15 is held distant from the proximal openings 61 of the syringe 6 when the finger flange 62 contacts the step 14. Thus, in this position the proximal opening 61 and the interior of the syringe 6 are open and accessible. The device 1 is in a distant position.

In the step of FIG. 2E the syringe 6 is transferred by the transporter of the first facility to a freeze-drying block 7 of a freeze-dryer of the first facility. Thereby, the device 1 still is in the distant position. The freeze-drying block 7 is made of aluminium and has plural receptacles 71. Each receptacle 71 is embodied as a bore with a profile shaped to receive one syringe 6. In particular, the profiles of the receptacles 71 have a lower needle section 711 dimensioned to receive the needle together with the rigid needle shell 64 of the syringe 6 and an upper body section 713 dimensioned to contact the lower part of the body portion 63 of the syringe 6. Between the needle section 711 and the body section 713 a shoulder section 712 is formed which is dimensioned to receiving the distal end side of the syringe 6. The top side of the body section 713 passes over into a conical entrance section 714 which allows for conveniently entering the syringe 6 into the receptacle 71.

When the syringe 6 is arranged in one of the receptacles 71 of the freeze-drying block 7, heat is provided via the side walls of the body portions 713 of the receptacles 71 and the side walls of the body portion 63 of the syringe 6 to the liquid substance being at the bottom of the body portions 63 of the syringe 6. Like this, the heat is conductively transferred to the substance and simultaneously the section of the body portion 63 of the syringe 6 where the substance is located is insulated with respect to heat irradiation. By conductively providing the heat to the substance a homogeneous heat transfer and lyophilisation is achieved. Furthermore, the isolation allows for preventing the substance being heated by irradiation during lyophilisation but, e.g., mainly by conductive heat transfer. Since the plunger 15 is held by the support of the device distant from the proximal opening 61 of the syringe 6 gas and steam escapes the syringe 6 via the proximal opening 61 during lyophilisation.

In the step of FIG. 2F, after lyophilisation of the substance, the support of the device 1 is lowered top down on the syringe 6 and the plunger 15 is connected to the proximal opening 61 of the syringe 6. The device now is in a near position. Since resulting from lyophilisation of the substance an underpressure is induced in the interior of the syringe 6 the plunger 15 is sucked into the syringe 6 and its interior is closed. Thereby, the plunger 15 is moved as far into the syringe 6 such that two chambers are formed inside the syringe 6 wherein the plunger 15 seals a distal chamber housing the lyophilised substance from a proximal chamber.

In step of FIG. 2G the syringe 6 is again positioned in the holder 4 as described above wherein the rigid needle shield 64 extends through the guiding rails 5. As shown in the step of FIG. 2H, the holder 4 together with the syringe 6 is then transferred along the guiding rails 5 by the transporter of the first facility to the feeding station of the first facility. There, a discharging pipe of a medium dosing feeder 92 of the first facility is entered through the though-hole 111 of the plunger seat 11 and the proximal opening 61 into the interior of the syringe 6. The medium dosing feeder 92 feeds a reconstitution medium or diluent in the proximal chamber of the syringe 6. After being fed, the reconstitution medium lies on the top of the plunger 15 inside the syringe 6, i.e., in its proximal chamber.

In the step of FIG. 2I a further plunger is pressed into the proximal opening 61 of the syringe 6 by means of a tube 93 of a sealer of the first facility. Thereby, the proximal opening 61 of the syringe 6 is sealed by the further plunger. The syringe 6 is arranged in the guiding rails 5 wherein the distal end side of the body portion 63 abuts the rails 5. Like this the pushing force induced on the syringe 6 by the tube 93 of the sealer is received by the guiding rails 5.

After the proximal opening 61 of the syringe 6 being sealed, the holder 4 together with the syringe 6 is transferred by the transporter to an optical inspection station of the first facility. There, the quality of the lyophilised substance is verified. In the step of FIG. 2J the finally prepared syringe 6 being ready to be delivered is shown.

As described hereinabove, the syringe 6 is arranged in an upright position throughout the complete preparation process. This allows for an efficient handling and processing.

Figure 3:
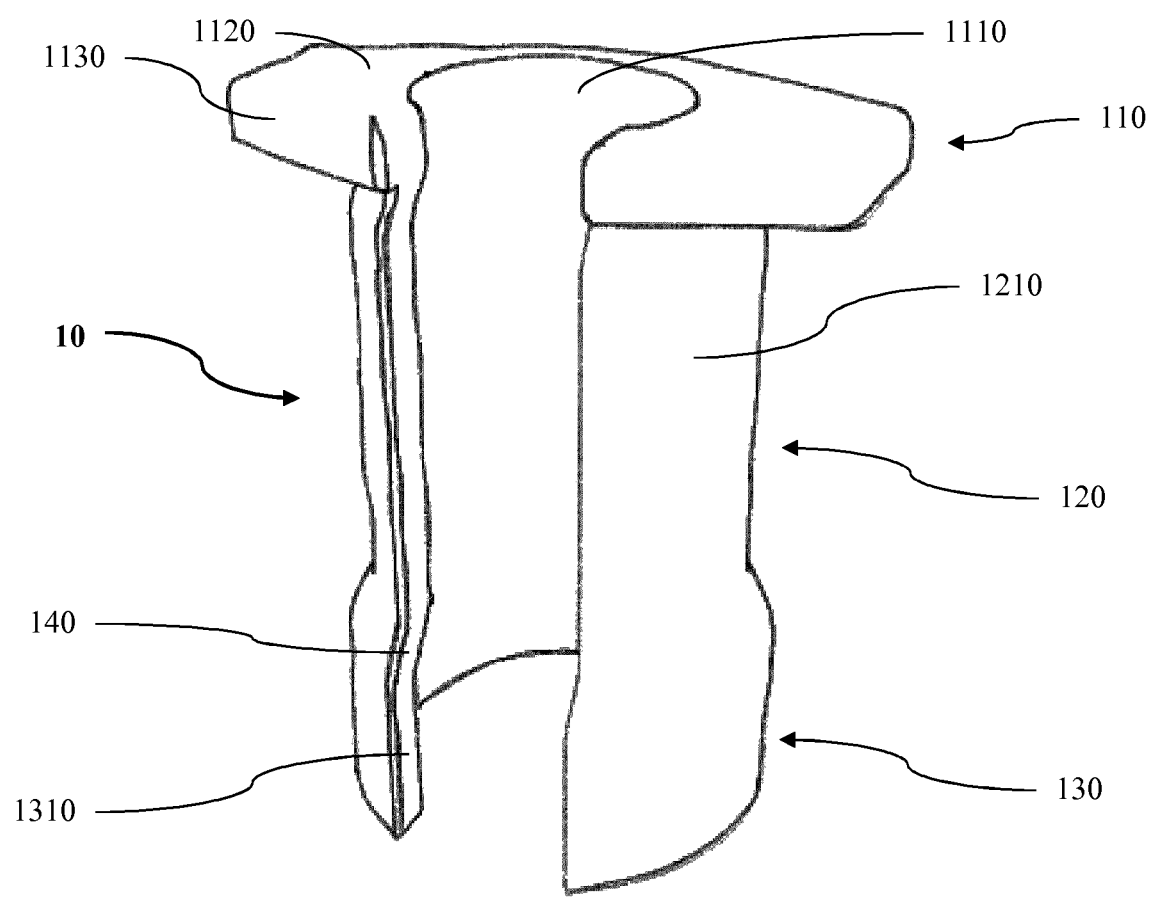
FIG. 3 shows a perspective view of a second embodiment of a device according to the invention.

In FIG. 3 a second embodiment of a device 10 according to the invention is shown. The device 10 comprises a support with a plunger seat 110, a container connector 130 as container carrier and a spacer 120 between the plunger seat 110 and the container connector 130. The support is embodied as one piece made from a plastic material. The plunger seat 110 is formed as a longitudinal plate 1120 of a constant thickness having plane top and bottom surfaces. In a top view the longitudinal plate 1120 widens towards its middle such that a central section of the plate 1120 has the largest width. In this central section of the longitudinal plate 1120 a central through-hole 1110 is arranged.

On its bottom surface the longitudinal plate 1120 passes over into the spacer 120. The spacer 120 comprises a hollow cylinder segment 1210 radially extending over about 270°. The cylinder segment 1210 surrounds a circular cylindrical interior. Each of two lateral sections of the longitudinal plate 1120 laterally project over the spacer 120 and, thereby, form a protrusion 1130.

On its bottom end, the cylinder segment 1210 of the spacer 120 passes over into a cylinder segment 1310 of a clamping portion of the container connector 130 via a step 140. The cylinder segment 1310 of the clamping portion of the container connector 130 also surrounds a circular cylindrical interior. The cylinder segment 1310 of the clamping portion of the container connector 130 has an inner diameter which is bigger than an inner diameter of the cylinder segment 1210 of the spacer 120. Thus, the step 140 outwardly extends from the cylinder segment 1210 of the spacer 120 to the cylinder segment 1310 of the clamping portion of the container connector 130.

Figure 4B:
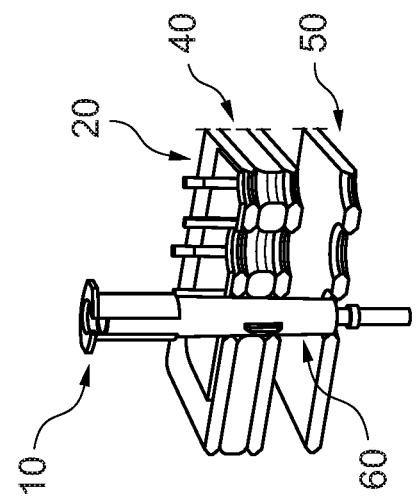
FIGS. 4BF'-4BK' show further perspective partial views of the facility of FIGS. 4AA'-4AE'.
Figure 4B:
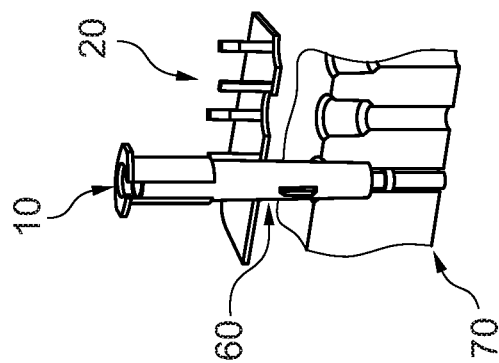
Figure 4B:
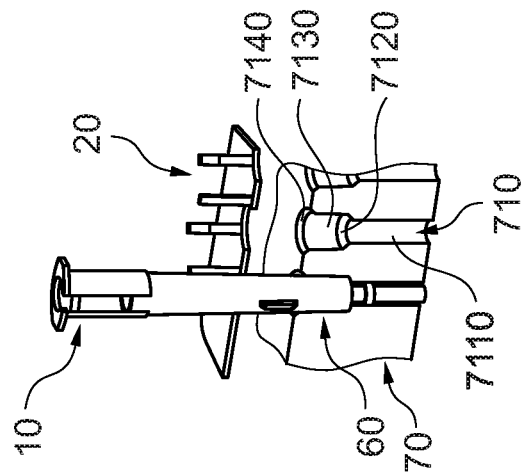
Figure 4B:
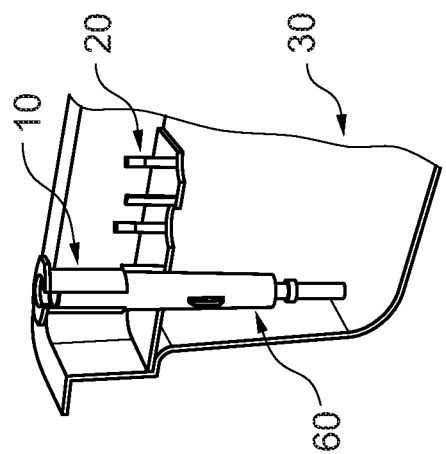
Figure 4B:
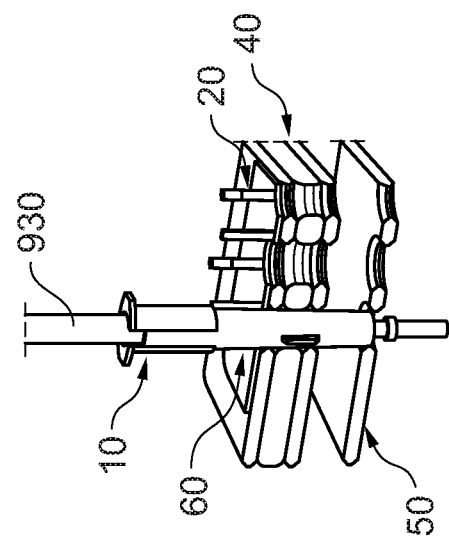
Figure 4B:
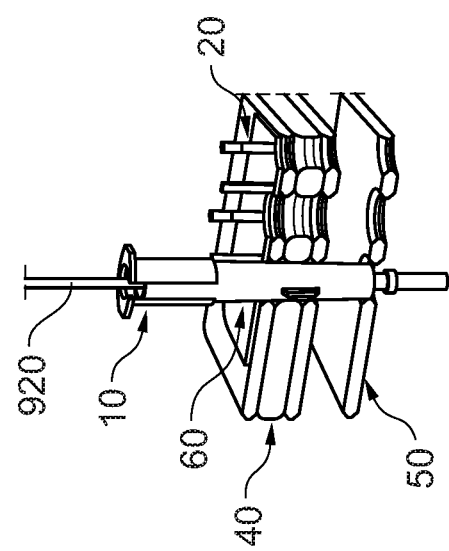

FIGS. 4AA'-4AE' and FIGS. 4BF'-4BK' show steps of a second embodiment of a method for preparing a second embodiment of a double chamber staked-in needle syringe 60 as container. The second method is implemented in a second embodiment of a facility for preparing the syringe 60. The syringe 60 has a distal end side, a proximal end side opposite to the distal end side and a cylindrical body portion 630 with an interior between the distal end side and the proximal end side. A distal opening provided with a needle is arranged at the distal end side. The needle is covered and protected by a rigid needle shell 640.

The proximal end side of the syringe 60 has a proximal opening 610. The distal end side, the body portion 630 and the proximal end side are integrally made of glass, i.e. are one piece. In a side wall of the body portion 630 a longitudinal vertical bulge is arranged as a bypass 620.

In the step of FIG. 4 AA' of the second method a set of identical syringes 60 is obtained in a tub 30. Each syringe 60 is arranged in a respective seat 210 of a holder 20. The holder 20 has a rectangular base plate 220 from which the seats 210 vertically and upwardly extend in the form of clamping fingers. The syringe 60 vertically extends through the seats 210 wherein the clamping fingers of the seat 210 are shaped and dimensioned to clamp and hold the syringe 60.

The tub 30 has a top border 310, a wider upper section 320 and a narrower lower section 340. Between the upper section 320 and the lower section 340 a shoulder section 330 is formed. When being arranged in the tub 30, the base plate 220 of the holder lies on the shoulder section 330 of the tub 30. Thereby, the seats 210 and the portions of the syringe 60 being in the seats 210 lie in the upper section 320 of the tub 30 and the rest of the syringes 60 in the lower section 340 of the tub 30. For transporting the tub 30 together with plural identical syringes 60, for example for delivering the syringes 60 to a suitable facility for preparing the syringes 60, the interior of the tub 30 can be sealed by a foil being bonded to the border 310 of the tub 30. Like this, the syringes 60 can be handled in a protected and sterile fashion.

In the step of FIG. 2 AB' of the first method the holder 20 together with the syringes 60 is transferred by a transporter of the second facility from the tub 30 to an alignment device 40 of the second facility. The transporter can be a robot such as a linear robot or an arm robot or the like. The alignment device 40 comprises a central main plate 420 with flat top and bottom surfaces, an upper alignment plate 410 on the top surface of the main plate 420 and a lower alignment plate 430 on the bottom surface of the main plate 420. The upper alignment plate 410 has a plurality of though bores 4110 corresponding to the arrangement of the seats 210 of the holder 20, the main plate 420 has respective through bores 4210 and the lower alignment plate 430 has respective through bores 4310. Adjacent through bores 4110, 4210, 4310 of the upper alignment plate 410, the main plate 420 and the lower alignment plate 430 together form adjustment openings of the alignment device 40.

For arranging the syringes 60 in the alignment device 40 the holder 20 is placed on a top surface of the upper alignment plate 410 such that each one of the seats 210 of the holder 20 is on top of an adjustment opening of the alignment device 40. Thereby, the syringes 60 extend through the adjustment openings of the alignment device 40. The upper alignment plate 410 and the lower alignment plate 430 are laterally movable along the top surface of the main body 420 or along the bottom surface of the main body 420, respectively. Like this, the syringes 60 can be precisely aligned by moving the upper and lower alignment plates 410, 430 of the alignment device 40 such that, e.g., substances can be exactly delivered into the syringes 60 as described in the following.

Furthermore, the syringes 60 are positioned in a centering plate 50 of the second facility while being arranged in the alignment device 40. The centering plate 50 has recesses 510 located in correspondence with the location of the seats 210 of the holder 20. Each recess 510 is embodied as a conical though hole formed such that the distal end sides of the syringes 60 can be received and held.

In the step of FIG. 2AC' a substance such as a liquid pharmaceutical substance or particularly a liquid biopharmaceutical substance is fed into the interior of each syringe 60. For this purpose, a discharge pipe of a substance dosing feeder 910 of the second facility is entered through the proximal opening 630 into the interior of the respective syringe 60. Then the substance is filled into the interior of the syringe 60 wherein the syringe 60 is precisely aligned by the alignment device 40 in order to prevent leakage and contamination. The substance is thereby lying on the bottoms of the interiors of the syringes 60, i.e. at the distal end sides of the syringes 60.

In the step of FIG. 4AD' the distance between the alignment device 40 and the centering plate 50 is reduced. Thereby, the syringes 60 are vertically lifted with respect to the alignment device 40 such that larger sections of the body portions 630 of the syringes 60 are accessible above the seats 210 of the holder 20.

As shown in the step of FIG. 4AE', when being held and stabilized by the centering plate 50, on each syringe 60 one support of the devices 10 is imposed. In the through-hole of each of the supports a rubber plunger 150 is arranged. Per syringe 60, the support of the device 10 is shifted as far top down on the body portion 630 of the syringe 60 that the step 140 abuts and slightly clamps the upper edge of the body portion 630. Like this the support is held on the syringe 60. The device 10 is in a distant position.

Turning to the step of FIG. 4BF' the holder 20 together with the syringes 60 is transferred by the transporter of the second facility to a freeze-drying block 70 of a freeze-dryer of the second facility. Thereby, the syringes 60 are clamped in the seats 210 of the holder 20. The freeze-drying block 70 is made of aluminium and has receptacles 710 located in correspondence with the location of the seats 210 of the holder 20. Each receptacle 710 is embodied as a bore with a profile shaped to receive one of the syringes 60. In particular, the profiles of the receptacles 710 have a lower needle section 7110 dimensioned to receive the rigid needle shield 640 of one of the syringes 60 and an upper body section 7130 dimensioned to contact the distal end of the body portion 630 of the syringe 60. Between the needle section 7110 and the body section 7130 a shoulder section 7120 is formed which is dimensioned to receiving the distal end side of the body portion 630 of the syringe 60. The top side of the body section 7130 passes over into a conical entrance section 7140 which allows for conveniently entering the respective syringe 60 into the receptacle 710.

When the syringes 60 are arranged in the receptacles 710 of the freeze-drying block 70 heat is provided via the side walls of the body portions 7130 of the receptacles 710 and the side walls of the body portions 630 of the syringes 60 to the liquid substance being at the bottoms of the body portions 630 of the syringes 60. Like this, the substance inside the syringes 60 is lyophilised as described above for the step of FIG. 2E the first method.

In the step of FIG. 4BG', after lyophilisation of the substance, the supports of the devices 10 are lowered on the syringes 60 and the plungers 150 are connected to the proximal openings 630 of the syringes 60. The device 10 is now in a near position. Since the lyophilisation induces an underpressure in the interior of the syringes 60 the plungers 150 are sucked downwardly into the interior of the body portions 630 of the syringes 60. Thereby, the plungers 150 are arranged above the bypasses 620 of the syringes 60. Like this, two chambers are built in the interior of each syringe 60, i.e. one distal chamber comprising the lyophilised substance and one proximal chamber. The plungers 150 seal the proximal chambers from the distal chambers.

In the step of FIG. 4BH' the holder 20 together with the syringes 60 equipped with the supports of the devices 10 are transferred to and positioned in the aligning device 40 and the centering plate 50.

In the step of FIG. 4BI' a discharging pipe of a medium dosing feeder 920 of the second facility is entered through the proximal opening 610 into the interior of the respective syringe 60. The medium dosing feeder 920 feeds a reconstitution medium or diluent in the proximal chamber of the syringe 60 wherein the syringe 60 is precisely aligned by the alignment device 40. After being fed, the reconstitution medium lies on the top of the plungers 150 above the bypasses 620 of the body portions 630 of the syringes 60.

In the step of FIG. 4BJ' further plungers are pressed into the proximal openings 610 of the syringes 60 by means of tubes 930 of a sealer of the second facility. Thereby, the proximal openings 610 of the syringes 60 are sealed by the further plungers. The syringes 60 are still arranged in the centering plate 50 wherein the distal end side of the body portions 630 abut the recesses 510. Like this, the pushing force induced on the syringes 60 by the tubes 930 of the sealer is received by the centering plate 50.

After the proximal openings 610 of the syringes 60 being sealed, the holder 40 together with the syringes 60 is transferred by the transporter to an optical inspection station of the second facility. There, the quality of the lyophilised substance is verified.

In the step of FIG. 4BK' the verified syringes 60 are transferred in the holder 20 to a tub 30 identical to the tub 30 they have initially been delivered to the second facility. In the tub 30 the syringes 60 can be delivered or shipped for further processing such as selling or the like. As shown hereinbefore, the syringes 60 are arranged in the seats 210 of the holder 20 in an upright position throughout the complete preparation process. This allows for an efficient handling and processing of plural syringes 60 which can be particularly useful on an industrial level.

Figure 5:
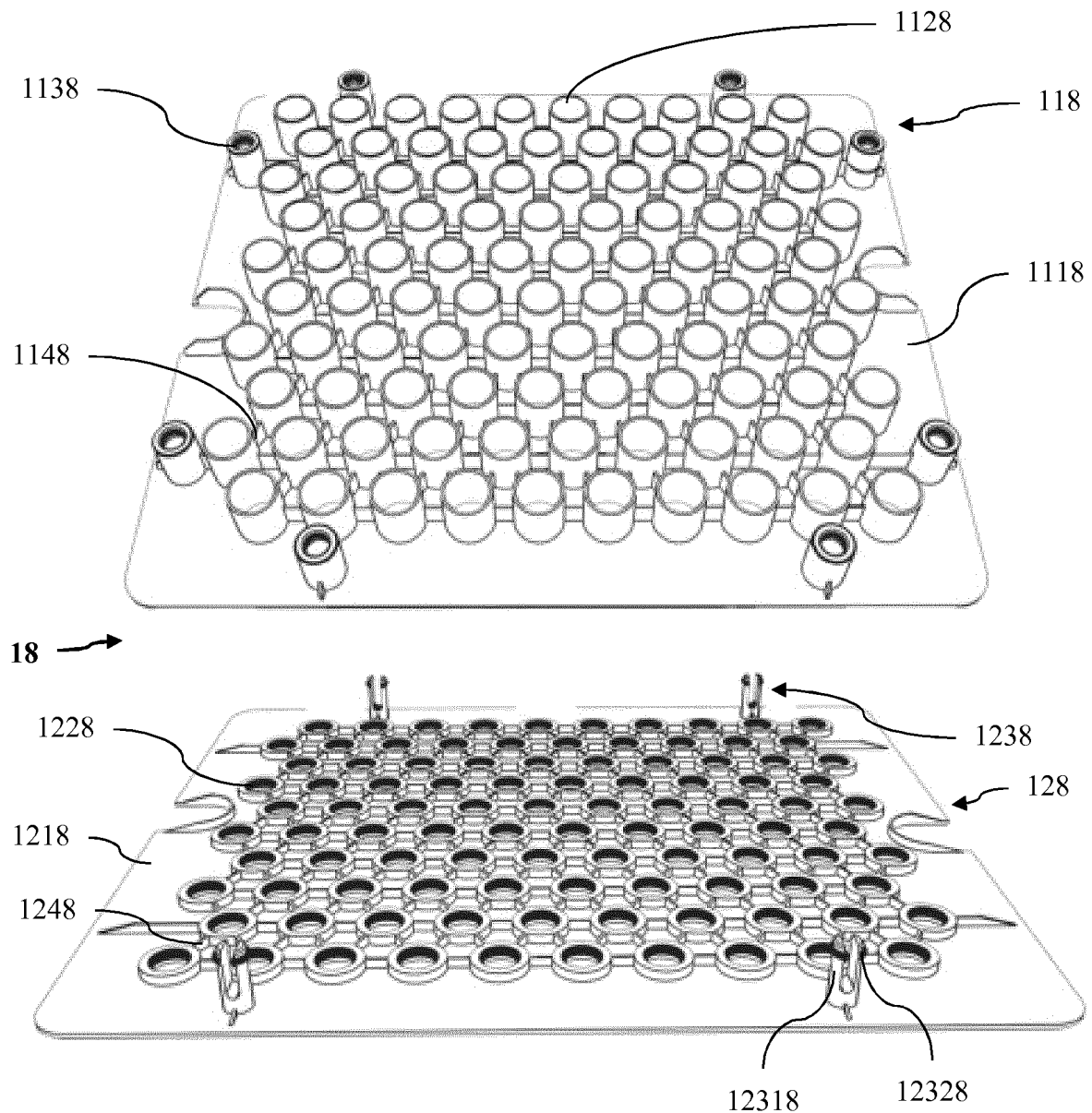
FIG. 5 shows a perspective view of a third embodiment of a device according to the invention.

In FIG. 5 a third embodiment of a device 18 according to the invention is shown. The device 18 comprises a holder 118 and a support 128. The holder 118 has an essentially squared holder base plate 1118 equipped with ten rows of ten syringe cavities 1128 as container carriers wherein each two neighbouring rows are offset to each other. Each syringe cavity 1128 is built as a vertical hollow cylinder extending from the holder base plate 1118. In order to stabilize the arrangement of the syringe cavities 1128 their cylinders are interconnected by ridges 1148. The holder 118 is arranged for providing a plurality of nested syringes.

Laterally beside the syringe cavities 1128 hollow cylinders of holder parts 1138 of spacers vertically extend from the base plate 1118 of the holder 118. In particular, two holder parts 1138 of the spacers are located near each of the sides of the base plate 1118 such that the holder 118 is equipped with eight holder parts 1138.

The support 128 comprises an essentially squared support base plate 1218 with through-holes as plunger seats 1228 being located in correspondence with the position of the syringe cavities 1128 of the holder 118. The through-holes have thickened rims which are interconnected by ridges 1248. Near two of the sides of the support base plate 1218 two support parts 1238 of the spacers are arranged. The four support parts 1238 are located in correspondence to the position of four of the holder parts 1138 of the holder 118.

Each of the support parts 1238 of the spacers comprises two opposing cylinder segments 12318 being separated by a free space. The cylinder segments extend vertically from the support base plate 1218. Near their top ends each cylinder segment 12318 of the support parts 1238 has a circumference bulge 12328 on its outer surface.

FIGS. 6A" to 6J" of a third embodiment of a method for preparing a third embodiment of a double chamber staked-in needle syringe 68 as container. The third method is implemented in a third embodiment of a facility for preparing the syringe 68. The syringe 68 is similarly shaped as the syringe described hereinbefore with respect to FIGS. 4AA'-4AE' and FIG. 4BF'-4BK'. In particular, it has an identical body portion 638 with a bypass 658 and a proximal opening 618, and a needle covered by a rigid needle shield 648. Different from the syringe 60 of FIGS. 4AA'-4AE' and FIGS. 4BF'-4BK', the syringe 68 comprises a finger flange 628 around the proximal opening 618 of the body portion 638.

In the step of FIG. 6A" of the third method a set of identical syringes 68 is obtained in a tub 38. The tub 38 is identically embodied as the tub 30 of FIGS. 4AA'-4AE' and FIGS. 4BF'-4BK'. In particular, it has an identical top border 318, an identical wider upper section 328 and an identical narrower lower section 348 wherein a shoulder section 338 is formed between the upper section 328 and the lower section 348.

Each syringe 68 is arranged in a respective syringe cavity 1128 of the holder 118 of the device 18. The syringes 68 vertically extend through the syringe cavities 1128 wherein the syringe cavities 1128 are dimensioned such that rigid needle shields 648, distal end sides and the body portions 638 of the syringes 68 fit though the hollow cylinders but not the finger flanges 628. Thus, the syringes 68 are arranged in the syringe cavities 1128 of the holder 118 by vertically hanging though the hollow cylinders wherein the finger flanges 628 lie on the top end of the hollow cylinders of the syringe cavities 1128.

When being arranged in the tub 38, the holder base plate 1118 of the holder 118 lies on the shoulder section 338 of the tub 38. Thereby, the syringe cavities 1128 and the portions of the syringes 68 being in the hollow cylinders lie in the upper section 328 of the tub 38 and the rest of the syringes 68 in the lower section 348 of the tub 38.

On the border 318 of the tub 38 the support 128 is arranged. Each plunger seat 1228 is equipped with one rubber plunger 158 which downwardly projects below the plunger seat 1228. Thereby, the through-holes of the plunger seats 1228 are dimensioned to releasably hold the plungers 158 by friction. Each plunger 158 is located adjacent to and distant from one of the proximal openings 618 of the syringes 68.

In the step of FIG. 6B" of the third method the nested plungers 158 are removed together with the support 128 from the tub 38 in order that the holder 118 with the nested syringes 68 is accessible.

In the step of FIG. 6C" the holder 118 together with the syringes 68 are transferred by a transporter of the third facility from the tub 38 to an alignment device 48 of the third facility. The transporter can be a robot such as a linear robot or an arm robot or the like. The alignment device 48 is identically embodied as the alignment device 40 described above in connection with FIGS. 4AA'-AE' and FIGS. 4BF'-BK'. In particular, it has an identical central main plate 428 with through bores 4218, an identical upper alignment plate 418 with through bores 4118 and an identical lower alignment plate 438 with through bores 4318.

For arranging the syringes 68 in the alignment device 48 the holder 118 is placed on a top surface of the upper alignment plate 418 such that each one of the syringe cavities 1128 of the holder 118 is on top of an adjustment opening of the alignment device 48. Thereby, the syringes 68 extend through the adjustment openings of the alignment device 48.

In the step of FIG. 6D" of the third method a substance such as a liquid pharmaceutical substance or particularly a liquid biopharmaceutical substance is fed into the interior of each syringe 68. For this purpose, a discharge pipe of a substance dosing feeder 918 of the third facility is entered through the proximal opening 638 into the interior of the respective syringe 68. Then the substance is filled into the interior of the syringe 68 wherein the syringe 68 is precisely aligned by the alignment device 48 in order to allow for preventing leakage and contamination. The substance is thereby lying on the bottoms of the interiors of the syringes 68, i.e. at the distal end sides of the syringes 68.

In the step of FIG. 6E" the support 128 together with the nested plungers 158 are placed on top of the holder 118. Thereby, the support parts 1238 of the spacers interengage with the holder parts 1138 of the spacers by clipping into a distant position as shown in more detail below. In this distant position the plungers 158 are exactly aligned distant from the proximal openings 618 of the syringes 68.

In the step of FIG. 6F" the holder 118 together with the syringes 68 and the support 128 are transferred by a transporter of the third facility to a freeze-drying block 78 of a freeze-dryer of the third facility. The freeze-drying block 78 is similarly embodied as the freeze drying block 70 of FIGS. 4AA'-4AE' and FIGS. 4BF'-4BK'. It is made of aluminium and has receptacles 718 located in correspondence with the location of the syringe cavities 1128 of the holder 118. Each receptacle 718 is embodied as a bore with a profile shaped to receive one of the syringes 68. In particular, the profiles of the receptacles 718 have a lower needle section 7118 dimensioned to receive the rigid needle shield 648 of one of the syringes 68 and an upper body section 7138 dimensioned to contact the distal end of the body portion 638 of the syringe 68. Between the needle section 7118 and the body section 7138 a shoulder section 7128 is formed which is dimensioned to receiving the distal end side of the body portion 638 of the syringe 68. The top side of the body section 7138 passes over into a conical entrance section 7148 which allows for conveniently entering the respective syringe 68 into the receptacle 718. Lyophilisation of the substance inside the syringes 68 by means of the freeze-drying block 78 is identically performed as explained with regard to the step of FIG. 2E of the first method.

In the step of FIG. 6G" of the third method, after lyophilisation of the substance, the support 128 of the device 18 is lowered on the holder 118 and the syringes 68. In particular, the support parts 1238 of the spacers are further clipped into the holder parts 1138 of the spacers as described in more detail below. The device 18 is now in a near position. Thereby, the plungers 158 are connected to the proximal openings 638 of the syringes 68. Since the lyophilisation induces an underpressure in the interior of the syringes 68 the plungers 158 are sucked downwardly into the interior of the body portions 638 of the syringes 68. At the end, the plungers 158 are arranged above the bypasses 628 of the syringes 68. Like this, two chambers are built in the interior of each syringe 68, i.e. one distal chamber comprising the lyophilised substance and one proximal chamber. The plungers 158 seal the proximal chambers from the distal chambers.

In the step of FIG. 6H" the holder 118 together with the syringes 60 and the support 128 are transferred to and positioned in the aligning device 48 again. Furthermore, the syringes 68 are positioned in a centering plate 58 of the second facility while being arranged in the alignment device 48. The centering plate 58 has recesses 518 located in correspondence with the location of the syringe cavities 1128 of the holder 118. Each recess 518 is embodied as a conical though-hole formed such that the distal end sides of the syringes 68 can be received and held.

In the step of FIG. 6I" the proximal chambers of the syringes 68 are provided with a reconstitution medium or diluent by means of a discharging pipe of a medium dosing feeder 928 of the third facility as described above in connection with the step of FIG. 4BI'. In the step of FIG. 6J" the interior of the body portions 638 of the syringes 68 are sealed by further plungers pushed in by means of tubes 938 of a sealer of the third facility as described above in connection with the step of FIG. 4BJ'.

Figure 7:
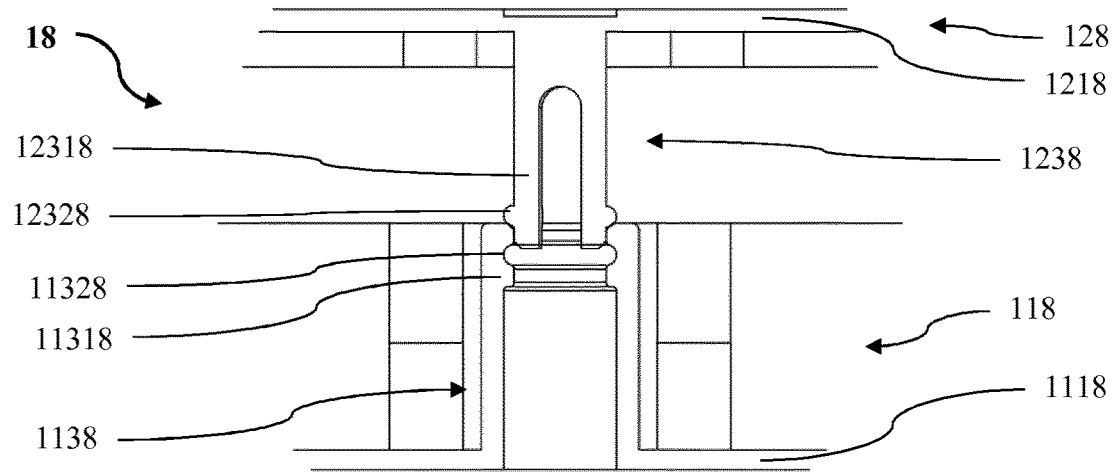
FIG. 7 shows a side view of a spacer of the device of FIG. 5 in a preliminary position.
Figure 8:
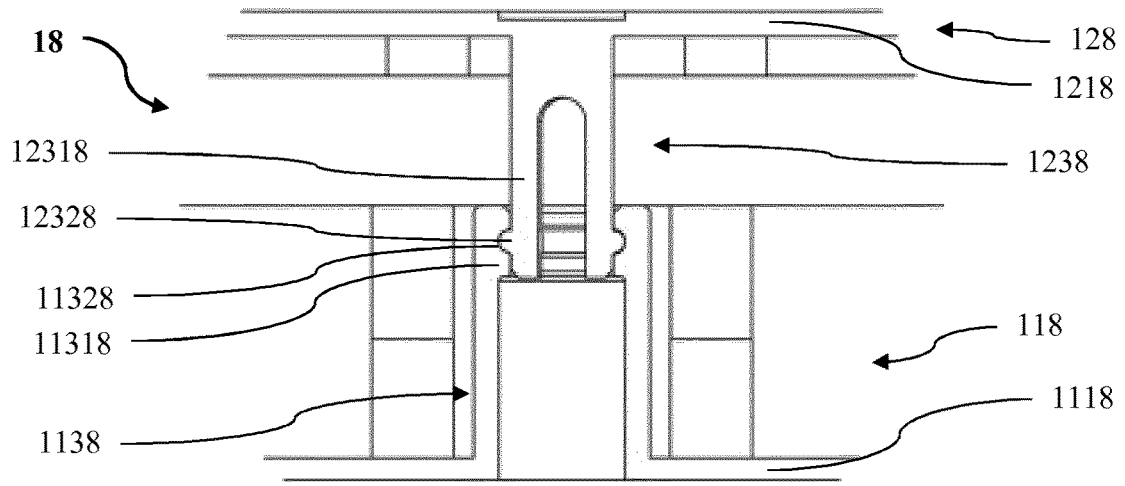
FIG. 8 shows a side view of the spacer of FIG. 7 in a distant position.
Figure 9:
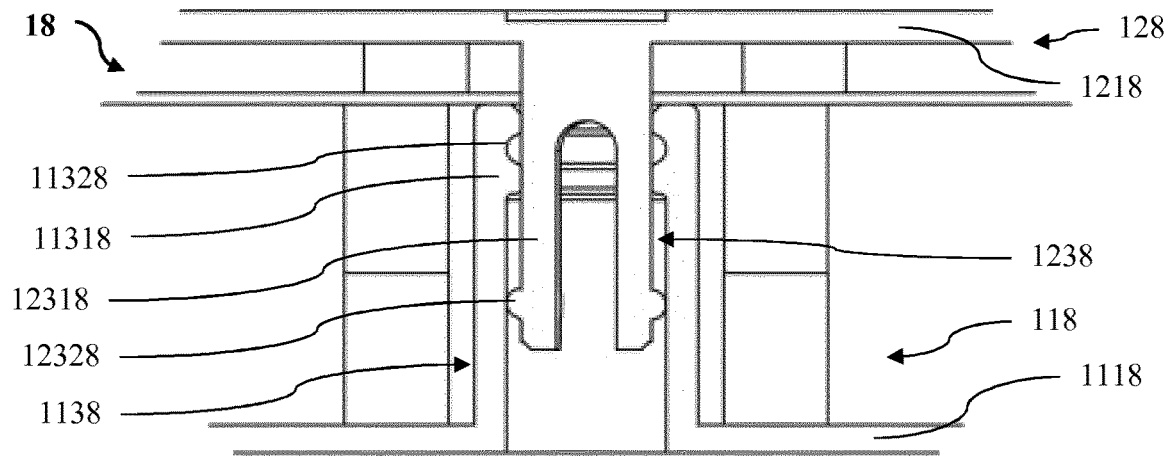
FIG. 9 shows a side view of the spacer of FIG. 7 in a near position.

FIG. 7, FIG. 8 and FIG. 9 show how the support parts 1238 of the spacer and the holder parts 1138 of the spacers interengage. As can be seen by the one support part 1238 and the one holder part 1138 shown in FIG. 7, in a preliminary position the support part 1238 is placed on top of the holder part 1138. In this position the sections of the cylinder segments 12318 being below the bulges 12328 are introduced into the top section 11318 of the hollow cylinder of the holder part 1138. The top section 11318 of the hollow cylinder has a thickened wall in which a circumferential groove 11328 is formed. In the preliminary position shown in FIG. 7 which is the position of the step of FIG. 6A" the support 128 and the holder 118 are aligned and held distant to each other but they are not connected. This allows that the holder 118 and the support 128 can easily be removed from each other as done in the step of FIG. 6B".

In FIG. 8 the spacer is shown in the distant position of the device 18. Thereby, the cylinder segments 12318 of the support part 1238 are clipped in the hollow cylinder of the holder part 1138 such that the bulges 12328 of the cylinder segments 12318 lie in the groove 11328 of the top section 11318 of the hollow cylinder. In this position the holder 118 and the support 128 are connected together wherein they still are distant from each other such that the plungers 158 and the syringes 68 do not contact each other. The holder 118 and the support 128 are in the distant position in the steps of FIGS. 6E" and 6F", particularly during lyophilisation.

FIG. 9 shows the spacer in the near position in which the cylinder segments 12318 of the support part 1238 are further advanced into the hollow cylinder of the holder part 1138. Like this the bulges 12328 of the cylinder segments 12318 engage behind the thickened top section 11318 of the hollow cylinder. In the near position the plungers 158 arranged in the plunger seats 1228 of the support 128 contact the proximal openings 618 of the syringes 68 arranged in the syringe cavities 1128 of the holder 118 (not shown in FIG. 9). The holder 118 and the support 128 are in the near position in the steps of FIGS. 6G", 6H", 6I" and 6J" of FIG. 6.

The steps of FIGS. 10A'" to 10J'" show a fourth embodiment of a method for preparing a fourth embodiment of a double chamber staked-in needle syringe 69 as container by using a fourth embodiment of a device 19 according to the invention. The fourth method is implemented in a fourth embodiment of a facility for preparing the syringe 69. The design of the syringe 69 is identical to the syringe 68 described above in connection with FIGS. 6A"-6J". In particular, each of the syringes 69 has an identical body portion 639 with a bypass 659 and a proximal opening 619 surrounded by a finger flange 629, and an identical needle covered by an identical rigid needle shield 649.

The device 19 comprises a holder 119 and a support 129. The holder 119 has an essentially squared holder base plate 1119 equipped with plural rows of syringe cavities 1129 as container carriers. Each syringe cavity 1129 is formed by a vertical hollow cylinder upwardly extending from the holder base plate 1119. Laterally beside the syringe cavities 1129 holder parts 1139 of spacers are arranged on the base plate 1119 of the holder 119.

The support 129 comprises an essentially squared support base plate 1219 with plunger through-holes 1229 as plunger seats being located in correspondence with the position of the syringe cavities 1129 of the holder 119. Near the sides of the support base plate 1219 support parts 1239 of the spacers are arranged at positions corresponding to the positions of the holder parts 1139 on the holder 119. Adjacent to each of the plunger through-holes 1229 an access through-hole 1249 is provided in the support base plate 1219 of the support 129.

In the step of FIG. 10A''' of the fourth method the holder 119 together with the syringes 69 and the support provided with rubber plungers 159 in the plunger through-holes 1229 are obtained in a tub 39. The tub 39 is identically embodied as the tub 30 of FIGS. 4AA'-4AE' and FIGS. 4BF'-4BK'. In particular, it has an identical top border 319, an identical wider upper section 329 and an identical narrower lower section 349 wherein a shoulder section 339 is formed between the upper section 329 and the lower section 349. The syringes 69 are vertically hanging in the syringe cavities 1129 as described above in connection with the step of FIG. 6A''. Also the holder 119 and the support 129 are arranged in the tub 39 as described above in connection with the step of FIG. 6A''.

In the step of FIG. 10B''' of the fourth method the holder 119 with the nested syringes 69 and the support 129 with the nested plungers 159 are together lifted out of the tub 39 and arranged in an alignment device 49 of the fourth facility. The alignment device 49 is identically embodied as the alignment device 40 described above in connection with FIGS. 4AA'-4AE' and FIGS. 4BF'-4BK'. In particular, it has an identical central main plate 429 with through bores 4219, an identical upper alignment plate 419 with through bores 4119 and an identical lower alignment plate 439 with through bores 4319.

The holder 119 and the support 129 are connected to each other in a distant position of the device 19 via the spacers. In this distant position the access through-holes 1249 of the support are located vertically above the proximal openings 619 of the syringes 69. Correspondingly, the plungers 159 are vertically offset with respect to the proximal openings 619 of the syringes 69.

For arranging the syringes 69 in the alignment device 49 the holder 119 is placed on a top surface of the upper alignment plate 419 such that each one of the syringe cavities 1129 of the holder 119 is on top of an adjustment opening of the alignment device 49. Thereby, the syringes 69 extend through the adjustment openings of the alignment device 49.

In the step of FIG. 10C''' of the third method a substance such as a liquid pharmaceutical substance or particularly a liquid biopharmaceutical substance is fed into the interior of each syringe 69. For this purpose, a discharge pipe of a substance dosing feeder 919 of the fourth facility is entered via the respective access opening 1249 of the support 129 through the proximal opening 619 into the interior of the respective syringe 69. Then the substance is filled into the interior of the syringe 69 wherein the syringe 69 is precisely aligned by the alignment device 49 in order to prevent leakage and contamination. By means of the access openings 1249 the interior of the syringes 69 can be straightly and efficiently reached by the discharge pipe of the substance dosing feeder 919.

In the step of FIG. 10D''' the holder 119 together with the syringes 69 and the support 129 are transferred by a transporter of the fourth facility to a freeze-drying block 79 of a freeze-dryer of the fourth facility. The freeze-drying block 79 is identically embodied as the freeze drying block 78 of FIGS. 6A'' to 6J''. It is made of aluminium and has identical receptacles 719 with a profile shaped to receive one of the syringes 69. In particular, the profiles of the receptacles 719 have an identical lower needle section 7119, an identical upper body section 7139, an identical shoulder section 7129 in between and an identical conical entrance section 7149. Lyophilisation of the substance inside the syringes 69 by means of the freeze-drying block 79 is identically performed as described with regard to the lyophilisation shown in FIGS. 4AA'-4AE' and FIGS. 4BF'-4BK' wherein the support 129 and the holder 119 are connected in the distant position.

In the step of FIG. 10E''' of the fourth method, after lyophilisation of the substance, the support 129 of the device 19 is lowered onto the holder 119 and the syringes 69. As explained in more detail below, by means of the spacers the support 129 is lowered diagonally onto the holder 119 to a near position such that in the near position each of the plungers 159 is located at a proximal opening 639 of one of the syringes 69. Thus, the distance between the support 129 and the holder 119 is reduced at the same time as they are laterally shifted to each other.

In the step of FIG. 10F''' the plungers 159 are connected to the proximal openings 639 of the syringes 69 in the near position of the spacers. There, an underpressure in the interior of the syringes 69 resulting from lyophilisation sucks the plungers 159 downwardly into the interior of the body portions 639 of the syringes 69. At the end, the plungers 159 are arranged above the bypasses 629 of the syringes 69 and two chambers are formed in the interior of each syringe 69, i.e. one distal chamber comprising the lyophilised substance and one proximal chamber.

Figure 10G:
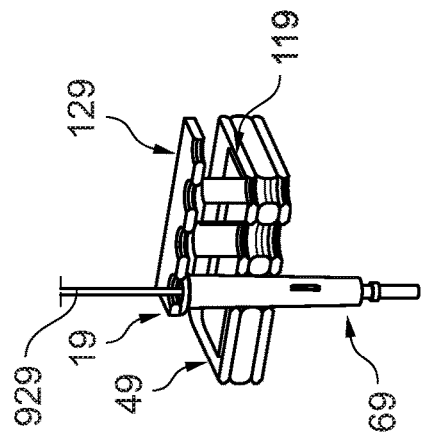
FIGS. 10A'"-10J'" show perspective partial views of a fourth embodiment of a facility for preparing a syringe using a fourth embodiment of a device according to the invention.
Figure 10H:
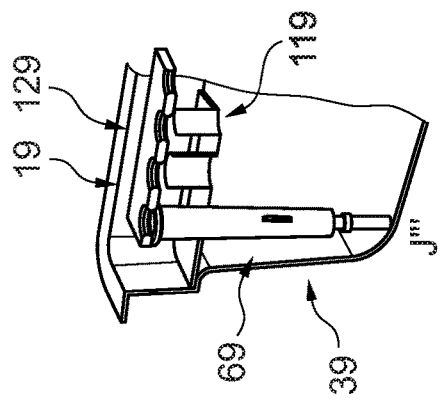

In the step of FIG. 10G''' of the fourth method the holder 119 together with the syringes 69 and the support 129 are transferred to and positioned in the aligning device 49 again. In the step of FIG. 10H''' the proximal chambers of the syringes 69 are provided with a reconstitution medium or diluent by means of a discharging pipe of a medium dosing feeder 929 of the fourth facility as described above in connection with the step of FIG. 4BI'.

Figure 10I:
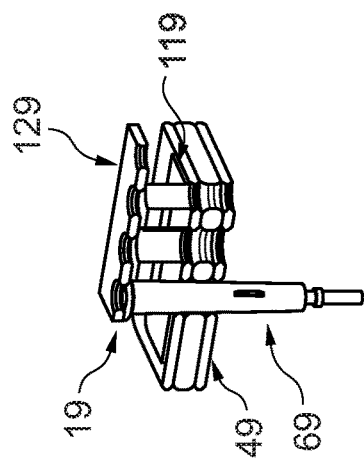

In the step of FIG. 10I''' the interior of the body portions 639 of the syringes 69 are sealed by further plungers pushed in by means of tubes 939 of a sealer of the fourth facility as described above in connection with the step of FIG. 4BJ'. Thereby, the pushing force induced by the tubes 939 is received by the alignment device 49 via the finger flanges 629 of the syringes 69 and the syringe cavities 1129 of the holder 119.

Figure 10J:
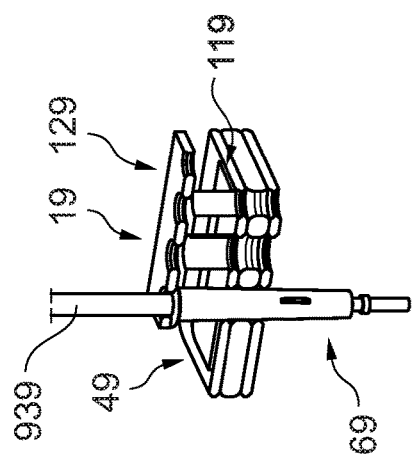

In the step of FIG. 10J''' the prepared syringes 69 are transferred in the holder 119 to a tub 39 identical to the tub 39 they have initially been delivered to the fourth facility. In the tub 39 the syringes 69 can be delivered or shipped for further processing such as selling or the like.

Figure 11:
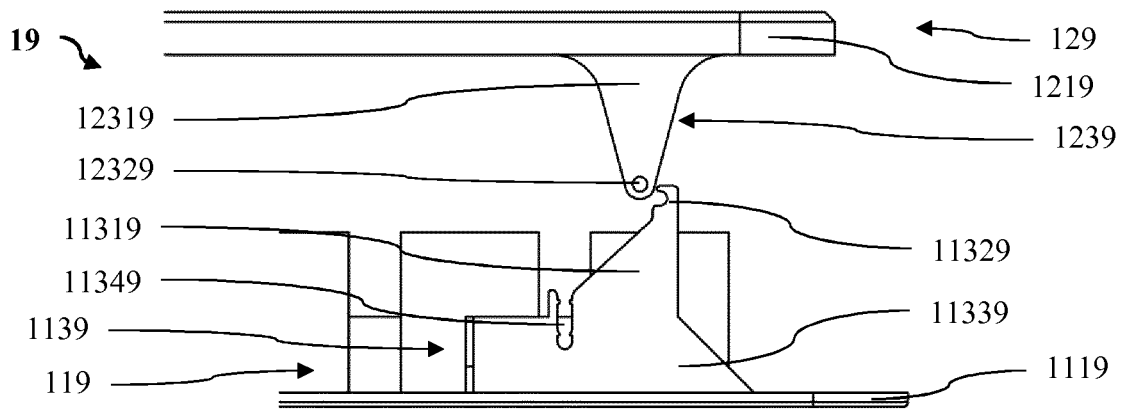
FIG. 11 shows a side view of a spacer of the device of FIGS. 10A'"-10J'" in a preliminary position.

FIG. 11 shows the spacer of the device 19 in an unconnected, separated or preliminary position. The preliminary position is present in the step of FIG. 10A'''. It comprises the support part 1239 and the holder part 1139. The support part 1239 has a slider mount 12319 which conically extends from the support base plate 1219. At a bottom portion of the slider mount 12319 a slider 12329 is connected which perpendicularly extends from the slider mount 12319. The slider 12329 is embodied as a post.

The holder part 1139 vertically extends from the holder base plate 1119 in an upward direction. It comprises a lower base section 11339 connected to the holder base plate 1119 from which a diagonal ramp 11319 upwardly extends. At a bottom end of the ramp 11319 a near fastener 11349 is embodied as recess in the base section 11339. At a top end, the ramp 11319 passes over into a distant fastener 11329 embodied as a C-shaped clamping hook.

Figure 12:
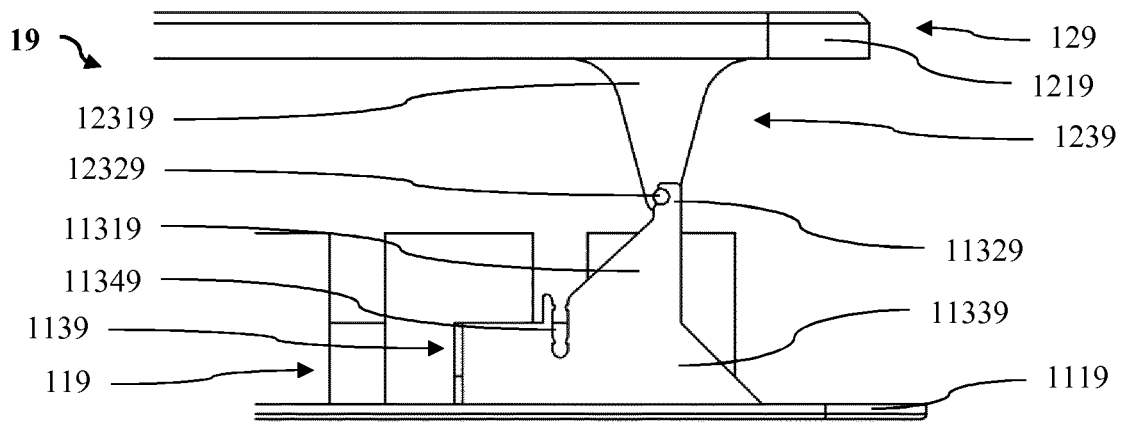
FIG. 12 shows a side view of the spacer of FIGS. 10A'"-10J'" in a distant position.

In FIG. 12 the spacer of the device 19 is shown in the distant position. In this position the slider 12329 is snapped in and clamped by the distant fastener 11329. Thus, the holder 119 and the support 129 are releasably connected to each other in the distant position. The distant position of the device 19 is present in the steps of FIGS. 10B''', 10C''' and 10D'''.

Figure 13:
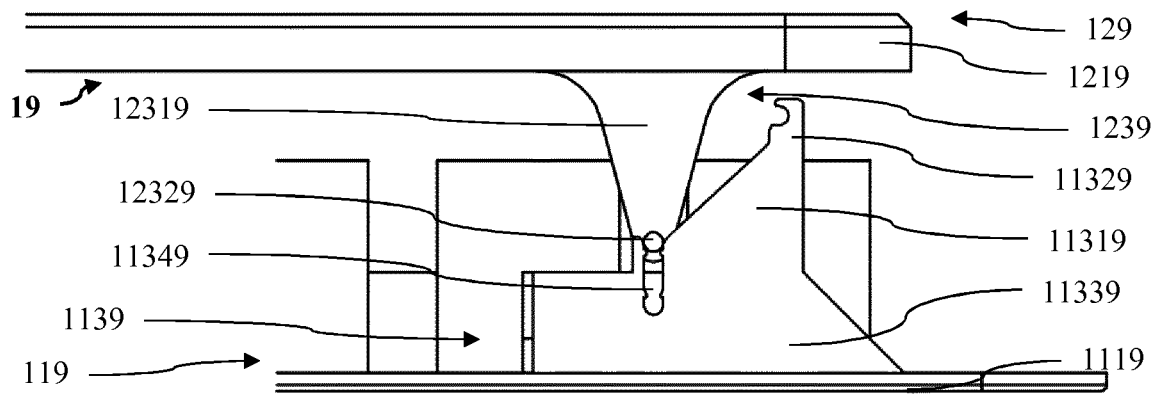
FIG. 13 shows a side view of the spacer of FIGS. 10A'"-10J'" in an intermediate position.

FIG. 13 shows the spacer of the device 19 after the slider 12129 is traveled downwardly along the ramp 11319. During such travel the support 129 is on one hand moved towards the holder 119 and on the other hand laterally shifted with respect to the holder 119.

Figure 14:
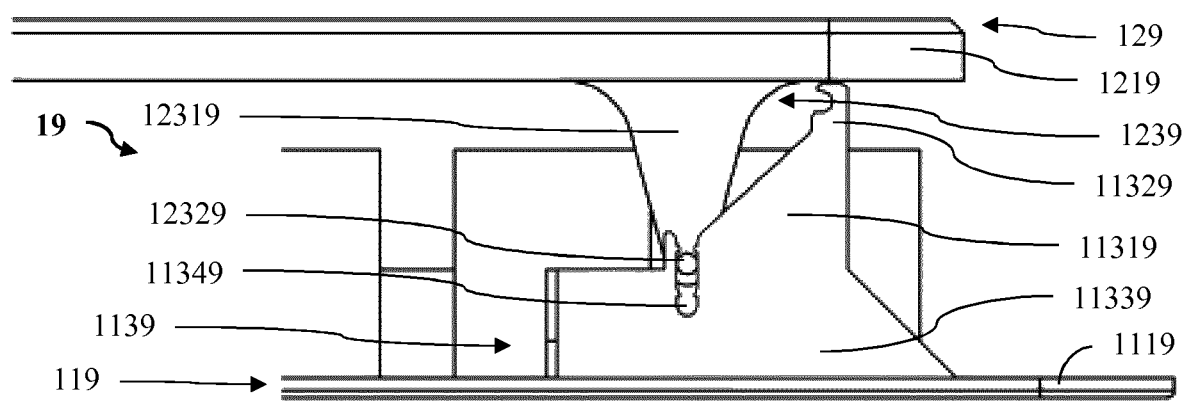
FIG. 14 shows a side view of the spacer of FIGS. 10A'"-10J'" in a near position.

In FIG. 14 the spacer is shown in the near position in which the slider 12129 is pressed into the near fastener 11349 in which it is clamped and secured. In this position the top of the distant fastener 11329 abuts the lower surface of the support base plate 1219. The near position is present in the steps of FIGS. 10E''' to 10J'''.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below. Various mechanical, compositional, structural, electrical, and operational changes may be made without departing from the spirit and scope of this description and the claims. In some instances, well-known circuits, structures, and techniques have not been shown in detail in order not to obscure the invention. Like numbers in two or more figures represent the same or similar elements.

The invention also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims ort the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

The invention claimed is:

1. A device for closing a chamber of a container having an opening for accessing the chamber, comprising:
    a plunger;
    a plunger seat comprising a plate with a through-hole;
    a container carrier comprising a step and a clamping portion for clamping a section of the container adjacent to the opening of the container; and
    a spacer, wherein
        the through-hole of the plunger seat releasably holds the plunger in a predefined alignment,
        the container carrier extends beneath the spacer and is arranged to be connected to the container in a predefined position and alignment in relation to the opening of the container,
        the spacer extends from beneath the plate of the plunger seat and is arranged to predefine a position and alignment of the plunger seat in relation to the container carrier,
        in a predefined distant position of the device, the plunger seat is located distant from the opening of the container when the container is connected to the container carrier such that the opening of the container is open, and
        in a predefined near position of the device, the plunger seat is arranged adjacent to the opening of the container when the container is connected to the container carrier such that the plunger is adapted to be provided into the opening of the container for closing the container, and
    wherein the spacer transitions into the clamping portion of the container carrier via the step, and wherein the step extends radially inward from the spacer to the clamping portion, and wherein the step is configured to contact a flange formed around the opening of the container.

2. The device according to claim 1, wherein the through-hole is dimensioned to releasably hold the plunger when being arranged in the through-hole.

3. The device according to claim 1, wherein the clamping portion of the container carrier comprises at least one cylinder segment between which the section of the container adjacent to its opening is clampable.

4. The device according to claim 3, wherein the spacer comprises at least one cylinder segment connecting the clamping portion of the container carrier via the step and the plunger seat.

5. The device according to claim 4, wherein each of the at least one cylinder segment of the clamping portion of the container carrier is connected to one of the at least one cylinder segment of the spacer via the step, and the at least one cylinder segment of the clamping portion has an inner diameter which is smaller than an inner diameter of the at least one cylinder segment of the spacer.

6. The device according to claim 4, wherein each of the at least one cylinder segment of the clamping portion of the container carrier is connected to one of the at least one cylinder segment of the spacer via the step, and the at least one cylinder segment of the spacer has an inner diameter which is smaller than an inner diameter of the at least one cylinder segment of the clamping portion.

7. The device according to claim 1, wherein the plunger seat comprises at least one protrusion laterally projecting over the spacer.

* * * * *